US009890106B2

(12) United States Patent
Sagar et al.

(10) Patent No.: US 9,890,106 B2
(45) Date of Patent: Feb. 13, 2018

(54) ANTI-CANCER LEAD MOLECULE

(71) Applicant: KING ABDULLAH UNIVERSITY OF SCIENCE AND TECHNOLOGY, Thuwal (SA)

(72) Inventors: Sunil Sagar, Thuwal (SA); Mandeep Kaur, Thuwal (SA); Luke E. Esau, Thuwal (SA)

(73) Assignee: KING ABDULLAH UNIVERSITY OF SCIENCE & TECHNOLOGY, Thuwal (SA)

( * ) Notice: Subject to any disclaimer, the term of this patent is extended or adjusted under 35 U.S.C. 154(b) by 461 days.

(21) Appl. No.: 13/802,430

(22) Filed: Mar. 13, 2013

(65) Prior Publication Data

US 2014/0107196 A1 Apr. 17, 2014

Related U.S. Application Data

(60) Provisional application No. 61/640,225, filed on Apr. 30, 2012.

(51) Int. Cl.
*A61K 31/235* (2006.01)
*A61K 45/06* (2006.01)
*C07C 69/157* (2006.01)
*A61K 31/05* (2006.01)
*A61K 31/122* (2006.01)
*A61K 31/136* (2006.01)
*A61K 31/192* (2006.01)
*A61K 31/222* (2006.01)
*A61K 31/277* (2006.01)
*A61K 31/495* (2006.01)

(52) U.S. Cl.
CPC ............ *C07C 69/157* (2013.01); *A61K 31/05* (2013.01); *A61K 31/122* (2013.01); *A61K 31/136* (2013.01); *A61K 31/192* (2013.01); *A61K 31/222* (2013.01); *A61K 31/235* (2013.01); *A61K 31/277* (2013.01); *A61K 31/495* (2013.01); *A61K 45/06* (2013.01)

(58) Field of Classification Search
USPC ......................................................... 514/546
See application file for complete search history.

(56) References Cited

U.S. PATENT DOCUMENTS

2009/0274746 A1* 11/2009 Gupta et al. .................. 424/430

FOREIGN PATENT DOCUMENTS

WO        2012018948 A2    2/2012
WO    WO 2012/08949      *    2/2012

OTHER PUBLICATIONS

Mathew et al (Inhibition of Mycobacterial Growth by Plumbagin derivatives, 2010, 76, pp. 34-42).*
Giridharan (Use of Animals in Scientific Research, 2000, pp. 1-27).*
Ahmad (Plumbagin-Induced Apoptosis of Human Breast Cancer Cells Is Mediated by Inactivation of NF-kB and Bcl-2, Journal of Cellular Biochemistry, 2008, 105, pp. 1461-1461.*
Tokunaga (Cytotoxic Antifeedant from Dionaea muscipula Ellis: A Defensive Mechanism of Carnivorous Plants against Predators, 2004, Bull Chem Soc Jpn, 77, pp. 537-541).*
Banditpuitat, J. et al.; Microwave-induced acetylation of 2-methyl-5-hydroxy-1,4-naphthoquinone (plumbagin). Maejo International Journal of Science and Technology 2009; vol. 3, No. 3, pp. 366-370.
Hazra, B. et al.; Synthesis of plumbagin derivatives andtheir iinhibitory activities against Ehrlich Ascites carcinoma in vivo and Leishmania donovani promastigotes in vitro. Medicinal & Aromatic Plants, Abstracts, Scientific Publishers, Scientific Publishers, New Delhi—India Dec. 1, 2002; vol. 24 No. 6.
Kuo, P.-L. et al.; Plumbagin induces G2-M arrest and autophagy by inhibiting the AKT/mammalian target ofrapamycin pathway in breast cancer cells. Molecular Cancer Therapeutics Dec. 1, 2006; vol. 5, No. 12, pp. 3209-3221.
Matthew, Ritta et al.; Inhibition of Mycobacterial Growth by Plumbagin Derivatives. Chemical Biiology & Drug Design May 18, 2010; vol. 76 No. 1, pp. 34-42.
Kanjoormana Aryan Manu et al.; Plumbagin inhibits invasion andmigration of breast and gastric cancer cells by downregulating the expression of chemokine receptor CXCR4. Molecular Cancer, Biiomed Central, London, GB Sep. 1, 2011; vol. 10 No. 1, pp. 107-121.
Sagar, Sunil et al.; Cytotoxicity and apoptosis induced by a plumbagin derivative in estrogen positive MCF-7 breast cancer cells. Anticancer Agents in Medicinal Chemistry 2014; vol. 14, pp. 170-180.
Kuo PL, et al. Plumbagin induces G2-M arrest and autophagy by inhibiting the AKT/mammalian target of rapamycin pathway in breast cancer cells. Mol Cancer Ther, 2006;5(12):3209-3221.
Aziz MH, et al. Plumbagin, a medicinal plant-derived napthoquinone, is a novel inhibitor of the growth and invasion of hormone refractory prostate cancer. Cancer Res, 2008;68(21):9024-9032.
Shih YW, et al. Plumbagin inhibits invasion and migration of liver cancer HepG2 cells by decreasing productions of matrix metalloproteinase-2 and urokinase-plasminogen activator. Hepatology Research, 2009;39:998-1009.
Srinivas P, et al. Plumbagin Induces Reactive Oxygen Species, Which Mediate Apoptosis in Human Cervical Cancer Cells. Molecular Carcinogenesis, 2004;40:201-211.

(Continued)

*Primary Examiner* — Kathrien Cruz
(74) *Attorney, Agent, or Firm* — Henry D. Coleman; R. Neil Sudol

(57) ABSTRACT

Derivatives of plumbagin can be selectively cytotoxic to breast cancer cells. Derivative 'A' (Acetyl Plumbagin) has emerged as a lead molecule for testing against estrogen positive breast cancer and has shown low hepatotoxicity as well as overall lower toxicity in nude mice model. The toxicity of derivative 'A' was determined to be even lower than vehicle control (ALT and AST markers). The possible mechanism of action identified based on the microarray experiments and pathway mapping shows that derivative 'A' could be acting by altering the cholesterol-related mechanisms. The low toxicity profile of derivative 'A' highlights its possible role'as future anti-cancer drug and/or as an adjuvant drug to reduce the toxicity of highly toxic chemotherapeutic'drugs.

6 Claims, 21 Drawing Sheets

(56) References Cited

OTHER PUBLICATIONS

Powolny AA, Singh SV. Plumbagin-induced Apoptosis in Human Prostate Cancer Cells is Associated with Modulation of Cellular Redox Status and Generation of Reactive Oxygen Species. Pharmaceutical Research, 2008;25(9):2171-2180.

Sreelatha T, et al. Synthesis and Insect Antifeedant Activity of Plumbagin Derivatives with the Amino Acid Moiety. J Agic Food Chem, 2009;57:6090-6094.

Ogihara K, et al. Preparation of Naphthoquinone Derivatives from Plumbagin and Their Ichthyotoxicity. Chem Pharm Bull, 1997;45(3):437-445.

Wurm G, et al. Lipophilic naphthols and 1,4-naphthoquinones as inhibitors of prostaglandin synthesis. 6. Study of 1,4-naphthoquinones. Arzneimittelforschung, 1984;34(6):652-658.

Van Summeren A, et al. Response to Pathophysiological Relevance of Proteomics Investigations of Drug-Induced Hepatotoxicity in HepG2 Cells. Toxicological Sciences, 2011;121(2):431-433.

Boone L, et al. Selection and interpretation of clinical pathology indicators of hepatic injury in preclinical studies. Vet Clin Pathol, 2005;34:182-188.

* cited by examiner

BJ treated with plumbagin and derivative 'A'

MCF-7 treated with plumbagin and derivative 'A'

(positive control = $H_2O_2$).

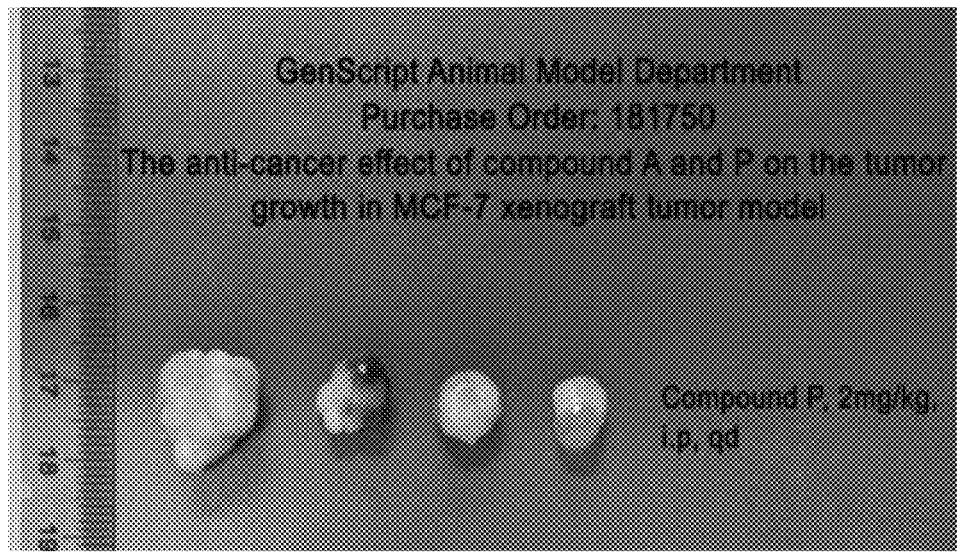
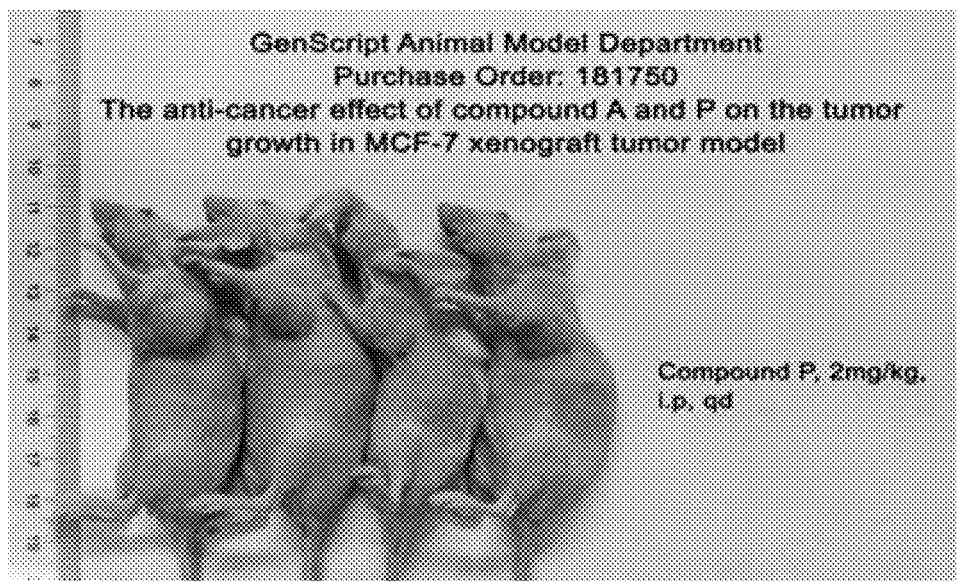
FIG. 6A

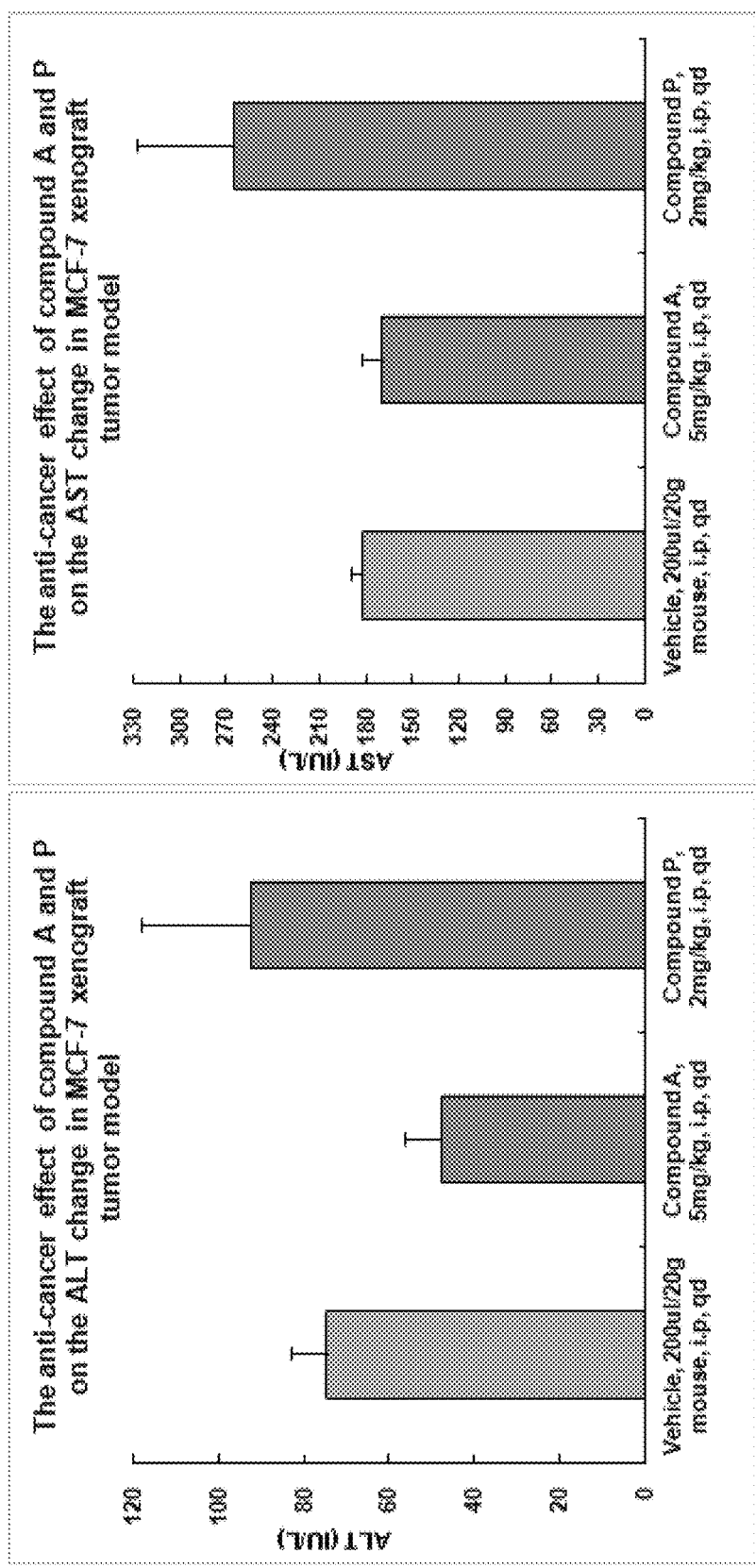

ANTI-CANCER LEAD MOLECULE

CLAIM OF PRIORITY

This application claims the benefit of prior U.S. Provisional Application No. 61/640,225, filed on Apr. 30, 2012, which is incorporated by reference in its entirety.

TECHNICAL FIELD

This invention relates to compounds that inhibit growth of breast cancer cells.

BACKGROUND

Breast cancer is one of worst diseases suffered by human beings. Due to the continuing development of drug resistance, there is always a need for the new drugs or lead molecules.

SUMMARY

Derivatives of plumbagin (5-hydroxy-2-methyl-1,4-naphthoquinone) are active and selective inhibitors of cell growth against the various human cancer cell lines. Certain substituted derivatives of plumbagin have been found to have selective activitiy for inhibiting growth or killing breast cancer cells. The activity is selective to cancerous cells over non-cancerous cell.

In one aspect, a method of treating breast cancer in a mammal includes administering to said mammal with an effective amount of a derivative of plumbagin, or a pharmaceutically acceptable salt thereof, represented by formula (I) or formula (II):

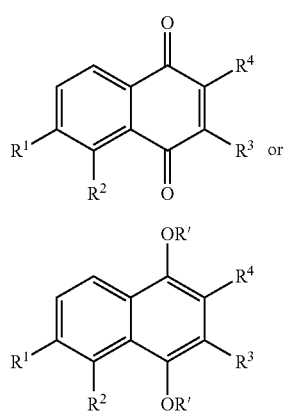

wherein $R^1$ is H, substituted or unsubstituted $C_1$-$C_{12}$alkyl, cyano, halo, carboxyl, or nitro;

$R^2$ is H, substituted or unsubstituted $C_1$-$C_{12}$alkyl, or O—R';

$R^3$ is H, substituted or unsubstituted $C_1$-$C_{12}$alkyl, —N(R')$_2$, or —O—R';

$R^4$ is H, —O—R', or $C_1$-$C_6$ alkyl; and each R', when present, independently, is H, substituted or unsubstituted $C_1$-$C_6$alkyl, or a hydolyzable moiety, such as acyl or trialkylsilyloxy.

In certain embodiments, $R^1$ can be H. In other embodiments, $R^2$ can be $R^a$—C(O)—O—, in which $R^a$ is methyl, ethyl, propyl, propenyl, isopropyl, butyl, isobutyl, sec-butyl, pentyl, hexyl, aryl or heteroaryl. In certain other embodiments, $R^3$ can be H. In other embodiments, $R^4$ can be H, —O—R', or $C_1$-$C_6$ alkyl. For example, $R^a$ can be phenyl. In other examples, $R^4$ can be H, OH, or methyl. In other examples, each group $R^1$-$R^5$, for each occurrence, can be, independently, optionally substituted with halo, carboxylic acid, cyano, or nitro.

In another aspect, a pharmaceutical composition can include the derivative of plumbagin, alone or in combination with another pharmaceutically active ingredient in which case the derivative of plumbagin can act as a pharmaceutical adjuvant. In certain embodiments, the composition can include one or more other pharmaceutical adjuvants or excipients.

Other features or advantages will be apparent from the following detailed description of several embodiments, and also from the appended claims.

BRIEF DESCRIPTION OF THE DRAWINGS

FIG. 2A shows BJ cells treated with plumbagin and derivative 'A'. FIG. 2B shows MCF-7 cells treated with plumbagin and derivative 'A'.

FIGS. 6A-6B are photographs of tumor mass of the group treated with plumbagin (FIG. 6A) or derivative 'A' (FIG. 6B), repectively.

FIG. 7A is comparison of the tumor weights of 3 mice groups. FIG. 7B is comparison of the tumor volumes of 3 mice groups.

FIGS. 8A-8B are graphs depicting the comparison of ALT (FIG. 8A) and AST (FIG. 8B) of mice groups after 21 days of treatment.

DETAILED DESCRIPTION

Figure 1A:
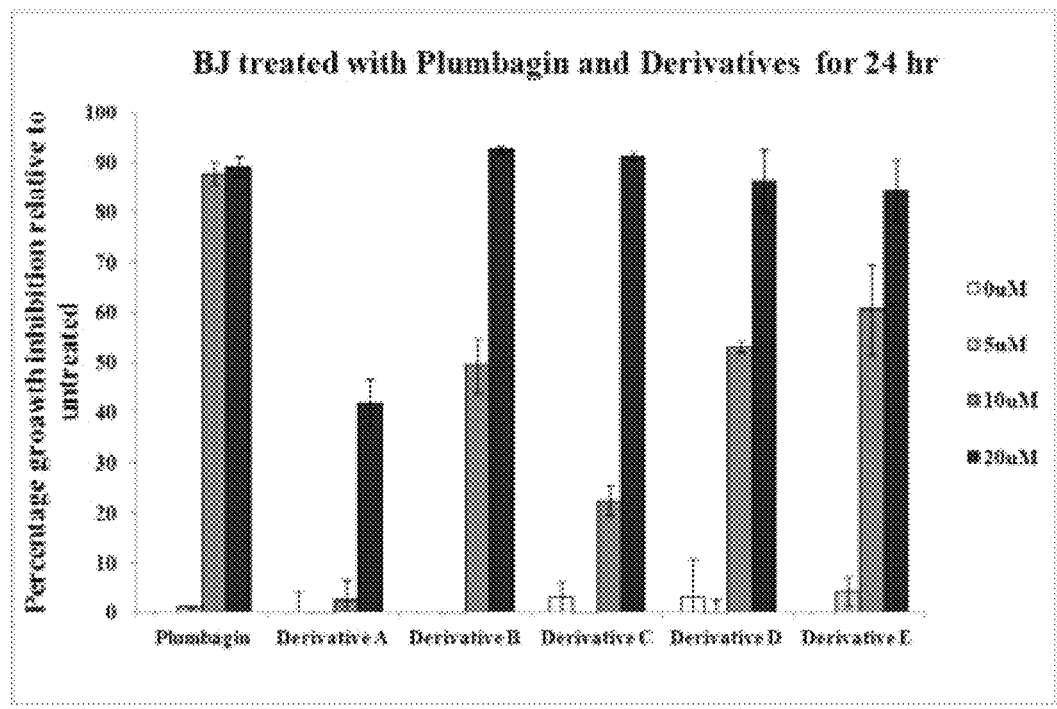
FIGS. 1A-FIG. 1E are a series of graphs depicting the effects of plumbagin and its derivatives (A, B, C, D and E) on cell proliferation of BJ (FIG. 1A), MCF-7 (FIG. 1B), BT20 (FIG. 1C), HepG2 (FIG. 1D) and DU145 (FIG. 1E) cell lines. Graphs represent cell growth inhibition in cell lines.
Figure 1B:
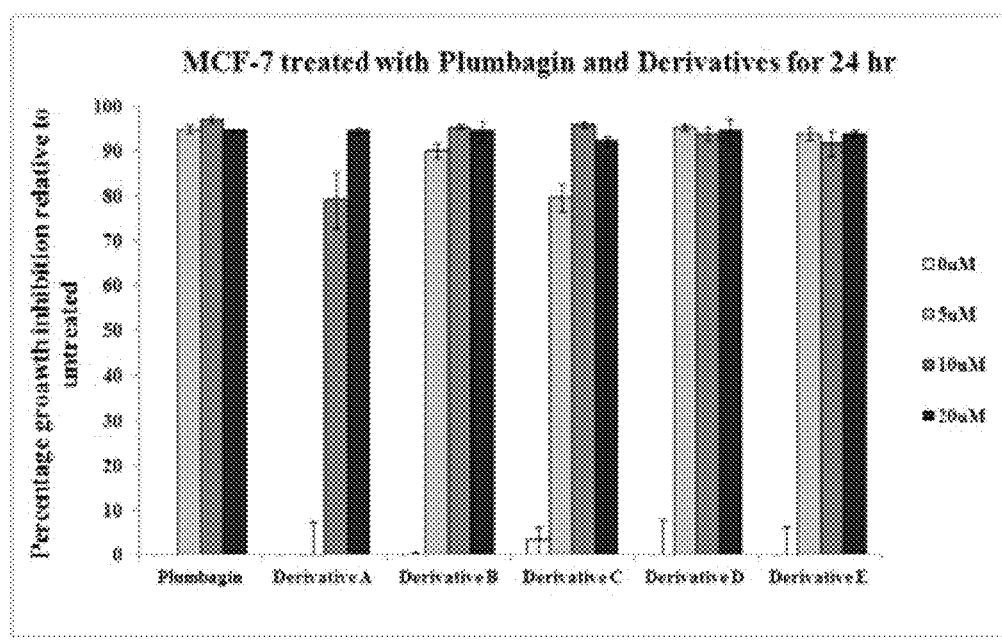
Figure 1C:
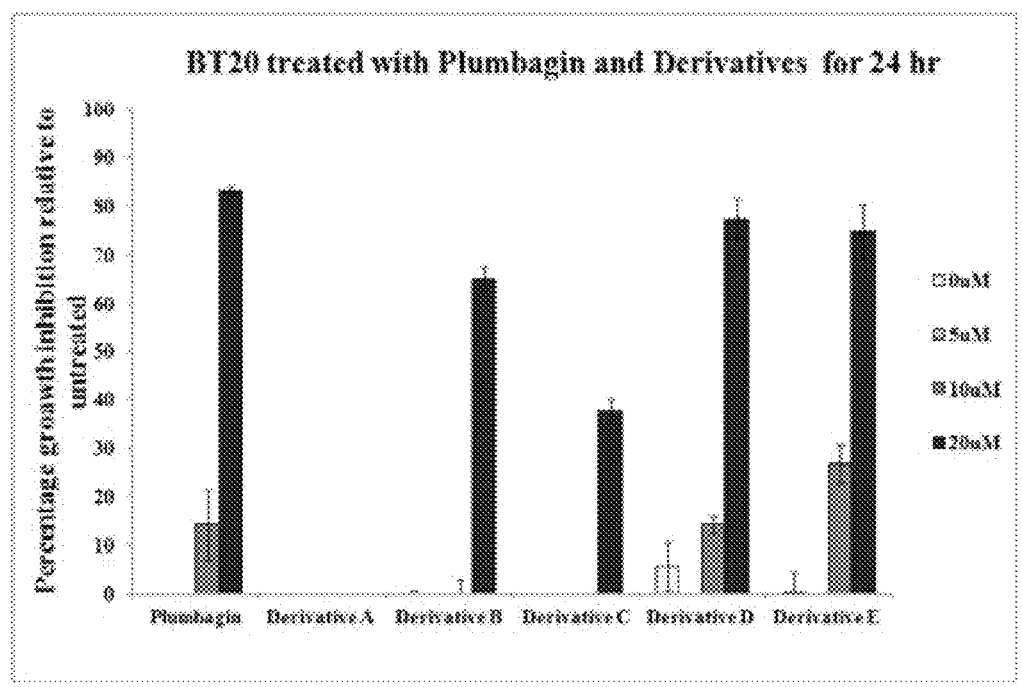
Figure 1D:
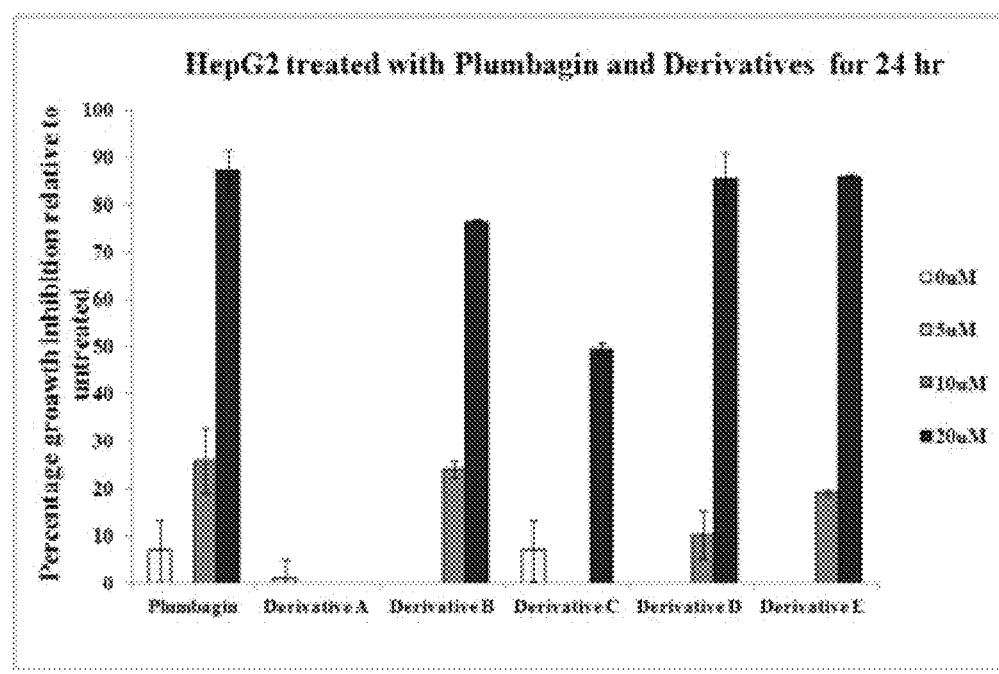
Figure 1E:
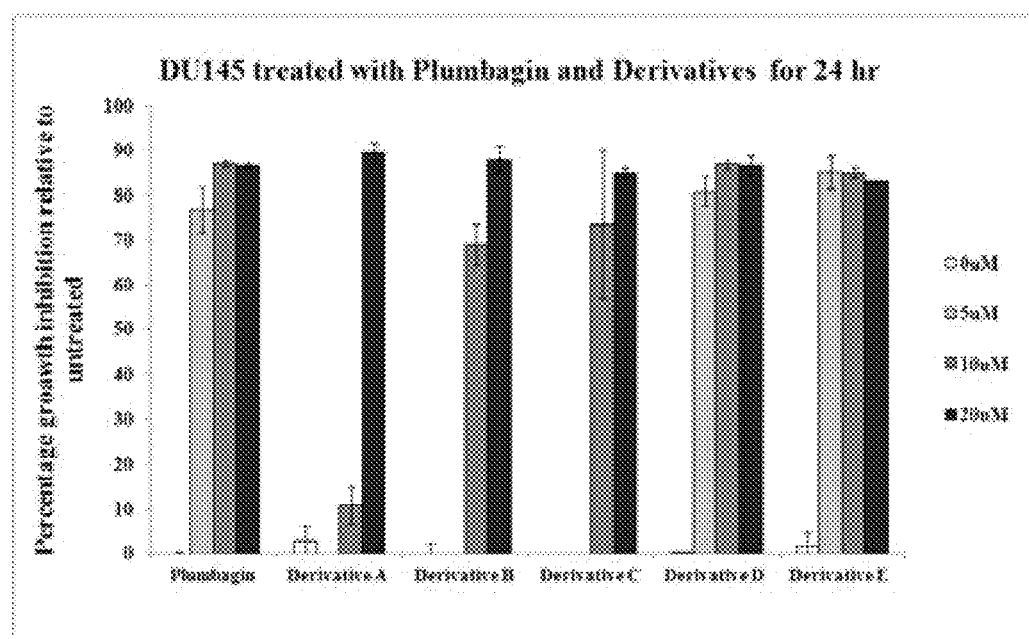

Plumbagin (5-hydroxy-2-methyl-1,4-naphthoquinone), a plant derived naphthoquinone, generally extracted from the roots of *Plumbago* species of three major phylogenetic families viz. Plumbaginaceae, Droseraceae, and Ebenceae, exhibits highly potent biological activities. The compound is well known for its general anti-cancer activity. See, for example, Kuo P L, et al. Mol Cancer Ther 2006, 5:3209-3221; Aziz M H, et al. Cancer Res 2008, 68:9024-9032; Shih Y W, et al. Hepatol Res 2009, 39:998-1009; Srinivas P, et al. Mol Carcinog 2004, 40:201-211; Powolny A A and Singh S V Pharm Res 2008, 25:2171-2180, each of which is incorporated by reference in its entirety. Since its first reported apoptotic activities, the compound has been envisaged as a "lead" molecule for the development of new therapeutic agents for cancer. Efforts have focused on the design and synthesis of novel analogues and derivatives of plumbagin which can exhibit better activity, reduced toxicity, or improved pharmokinetics.

The derivatives of plumbagin described here have been evaluated for apoptotic properties and have been shown to have unexpected selectivity compared to plumbagin itself. Examples of derivatives of plumbagin that have been synthesized include those prepared by Mathew et al. by following the general esterification methods, which were previously studied for their anti-tuberculosis activity. See, for example, Mathew R, et al. Chem Biol Drug Des 2010, 76:34-42, which is incorporated by reference in its entirety.

Derivatives of plumbagin can be tested for anti-cancer potential. Apoptotic potential of the derivatives and plumbagin are evaluated in five human cancer cell lines, such as HepG2 (liver carcinoma), HeLa (cervical carcinoma), MCF-7 (ER-positive) (breast carcinoma), BT-20 (ER-negative) (breast carcinoma) or DU145 (prostrate carcinoma), along with BJ (normal skin fibroblasts) in vitro using MTT and APOPercentage assays. Certain plumbagin derivatives showed significant selective cytotoxicity against cancer cell lines although normal cells (BJ) are unaffected even at higher concentration.

The derivatives of plumbagin can be cytotoxic to human breast cancer cells. By comparison to normal human cells, the compounds can be 2, 3, 4, 5, 8, 10, 15, 20 or more times less cytotoxic to normal human cells compared to human breast cancer cells. In certain embodiments, the $IC_{50}$ value of the disclosed compounds can be less than 20 micromolar, less than 15 micromolar, less than 10 micromolar, or less than 8 micromolar.

A derivative of plumbagin, or a pharmaceutically acceptable salt thereof, can be represented by formula (I) or formula (II):

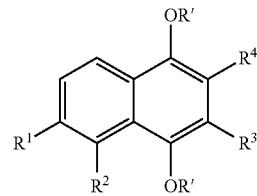

$R^1$ can be H, substituted or unsubstituted $C_1$-$C_{12}$alkyl, cyano, halo, carboxyl, or nitro.

$R^2$ can be H, substituted or unsubstituted $C_1$-$C_{12}$alkyl, or O—R'.

$R^3$ can be H, substituted or unsubstituted $C_1$-$C_{12}$alkyl, —N(R')$_2$, or —O—R'.

$R^4$ can be H, —O—R', or $C_1$-$C_6$ alkyl.

Each R', when present, independently, can be H, substituted or unsubstituted $C_1$-$C_6$alkyl, or a hydrolyzable moiety, such as acyl or trialkylsilyloxy.

In certain embodiments of the compound of formula (I), the double bond between $R^3$ and $R^4$ can be replaced with a single oxygen (to form an epoxy group) or H and CN, respectively.

In certain embodiments, $R^1$ is H.

In certain embodiments, $R^2$ is $R^a$—C(O)—O—, in which $R^a$ is methyl, ethyl, propyl, propenyl, isopropyl, butyl, isobutyl, sec-butyl, pentyl, hexyl, or phenyl.

In certain embodiments, $R^3$ is H.

In certain embodiments, $R^4$ can be H, —O—R', or $C_1$-$C_6$ alkyl.

In certain embodiments, $R^1$ is H and $R^3$ is H.

In certain embodiments, $R^2$ is $R^a$—C(O)—O—, in which $R^a$ is methyl, ethyl, propyl, propenyl, isopropyl, butyl, aryl or heteroaryl, for example, phenyl.

In certain embodiments, $R^4$ is H, OH, or methyl.

Each group $R^1$-$R^5$, for each occurrence, can be, independently, optionally substituted with halo, carboxylic acid, cyano, or nitro.

In other embodiments, the compound, or a pharmaceutically acceptable salt thereof, can be represented by one of the following formulae:

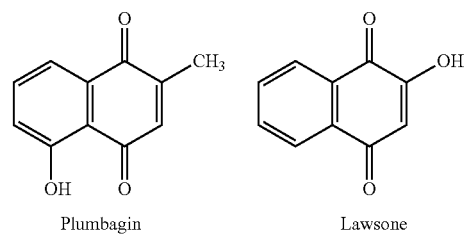

Plumbagin

Lawsone

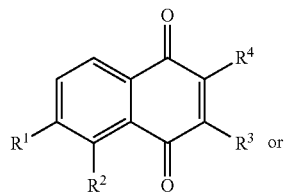

Juglone

Acetyl Plumbagin

-continued

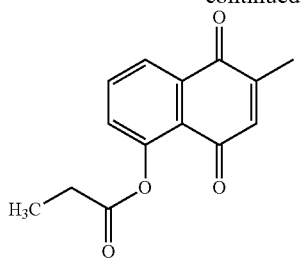
Propionate Plumbagin

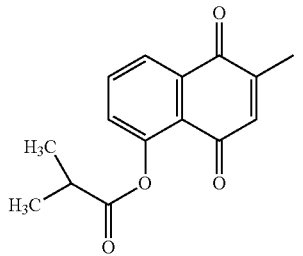
Isobutyrate Plumbagin

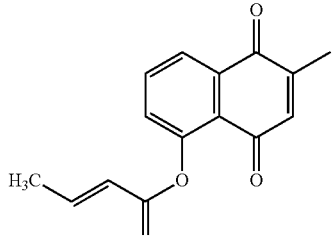
Crotonate Plumbagin

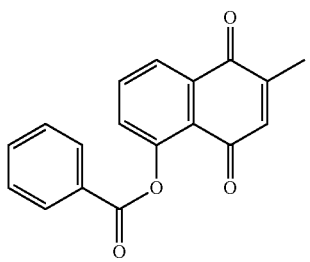
Benzoate Plumbagin

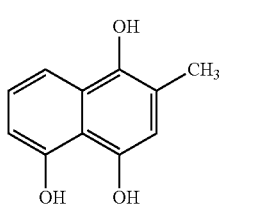
Hydroquinonoid derivative of plumbagin

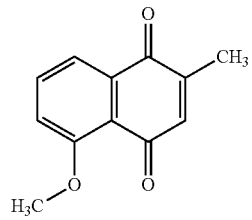
Methyl ester derivative of plumbagin

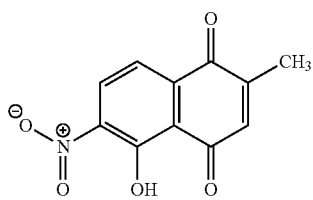
Nitro derivative of plumbagin

-continued

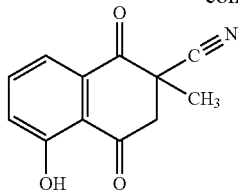
Cyano derivative of plumbagin

The hydroquinonoid, nitro, cyano, and methyl ester derivatives of plumbagin have been studied for their anti-tumor and anti-leishmanial activities. See, for example, Phytother Res 2002; 16:133-137, which is incorporated by reference in its entirety. These hydroquinonoid, nitro, cyano, and methyl ester derivatives of compounds can have unexpected benefits in treating certain cancers.

In another example, an amino acid moiety derivatives of plumbagin (formula (III)) have been synthesized and subsequently screened for antifeedant activity in tobacco caterpillar (*Spodoptera litura*) and castor semi-looper (*Achaea janata*). See, for example, J Agric Food Chem 2009; 57:6090-6094, which is incorporated by reference in its entirety. These amino acid moiety derivatives of plumbagin can have unexpected benefits in treating certain cancers.

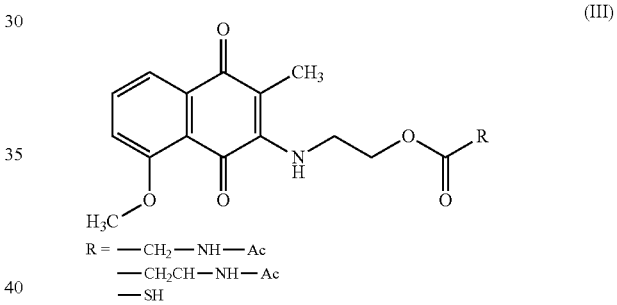

(III)

$R = -CH_2-NH-Ac$
$-CH_2CH-NH-Ac$
$-SH$

In another example, a derivative compound can be a naphthoquinone derivatives of plumbagin, which were mostly substituted at C-3 position through carbon-carbon bond formation, synthesized and screened for their ichthyotoxicity. See, for example, Chem Pharm Bull 1997; 45:437-445, which is incorporated by reference in its entirety. These naphthoquinone derivatives of plumbagin can have unexpected benefits in treating certain cancers. See, for example, formula (IV), formula (V) or formula (VI).

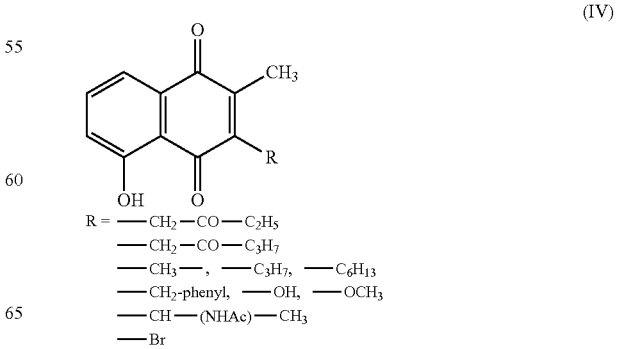

(IV)

$R = -CH_2-CO-C_2H_5$
$-CH_2-CO-C_3H_7$
$-CH_3-, -C_3H_7, -C_6H_{13}$
$-CH_2-phenyl, -OH, -OCH_3$
$-CH-(NHAc)-CH_3$
$-Br$

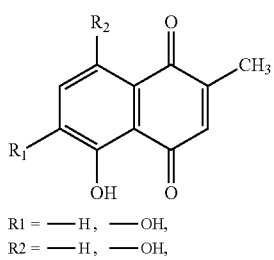

(V)

R1 = —H, —OH,
R2 = —H, —OH,

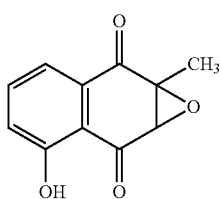

(VI)

In some embodiments, the derivative of plumbagin can be a plumbagin homologue (2-alkyl-1,4-naphthoquinones), including a 3-methyl derivative, which has also been synthesized to evaluate their prostaglandin synthetase (PGS)-inhibition activity. See, for example, Arzneimittelforschung 1984; 34:652-658, which is incorporated by reference in its entirety. These plumbagin homologues can have unexpected benefits in treating certain cancers. See, for example, formula (VII), formula (VII), formula (IX), formula (X), or formula (XI).

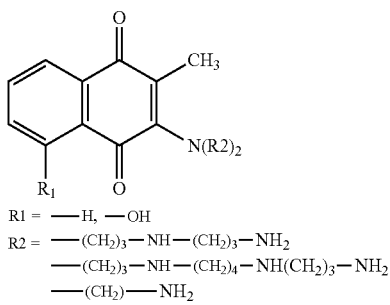

(VII)

R1 = —H, —OH
R2 = —(CH$_2$)$_3$—NH—(CH$_2$)$_3$—NH$_2$
—(CH$_2$)$_3$—NH—(CH$_2$)$_4$—NH(CH$_2$)$_3$—NH$_2$
—(CH$_2$)—NH$_2$

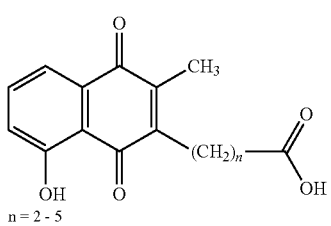

(VIII)

n = 2 - 5

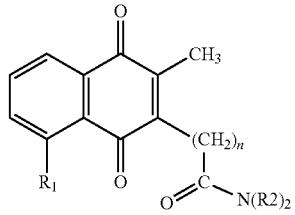

(IX)

n = 2 - 3
R1 = —H, —CH$_3$
R2 =

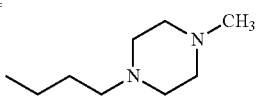

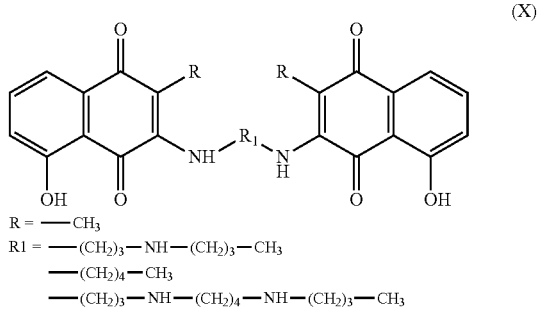

(X)

R = —CH$_3$
R1 = —(CH$_2$)$_3$—NH—(CH$_2$)$_3$—CH$_3$
—(CH$_2$)$_4$—CH$_3$
—(CH$_2$)$_3$—NH—(CH$_2$)$_4$—NH—(CH$_2$)$_3$—CH$_3$

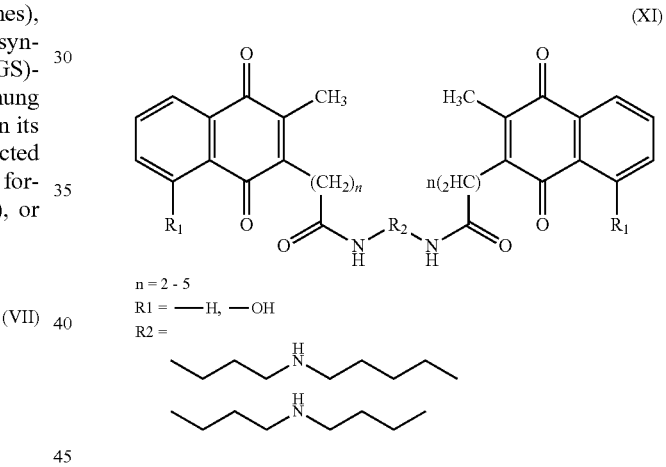

(XI)

n = 2 - 5
R1 = —H, —OH
R2 =

A salt of any of the compounds can be prepared. For example, a pharmaceutically acceptable salt can be formed when an amino-containing compound of this invention reacts with an inorganic or organic acid. Some examples of such an acid include hydrochloric acid, hydrobromic acid, hydroiodic acid, sulfuric acid, phosphoric acid, p-bromophenylsulfonic acid, carbonic acid, succinic acid, citric acid, benzoic acid, and acetic acid. Examples of pharmaceutically acceptable salts thus formed include sulfate, pyrosulfate bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, tosylate, methanesulfonate, acetate, citrate, malonate, tartarate, succinate, benzoate, ascorbate, α-ketoglutarate, α-glycerophosphate, sulfate, nitrate, bicarbonate, or carbonate salts. A compound described herein may also form a pharmaceutically acceptable salt when a compound having an acid moiety reacts with an inorganic or organic base. Such salts include those derived from inorganic or organic bases, e.g., alkali metal salts such as sodium, potassium, or lithium salts; alkaline earth metal salts such as calcium or magnesium salts; or ammonium salts or salts of organic bases such as morpholine, piperidine, pyridine, dimethylamine, or diethylamine salts.

It should be recognized that a suitable compound can contain chiral carbon atoms. In other words, it may have optical isomers or diastereoisomers.

Alkyl is a straight or branched hydrocarbon chain containing 1 to 12 (preferably, 1 to 6; more preferably 1 to 4) carbon atoms. Examples of alkyl include, but are not limited to, methyl, ethyl, propyl, isopropyl, butyl, isobutyl, sec-butyl, tert-butyl, n-pentyl, 2-methylhexyl, and 3-ethyloctyl.

Aryl is an aromatic group containing a 5-14 member ring and can contain fused rings, which may be saturated, unsaturated, or aromatic. Examples of an aryl group include phenyl, naphthyl, biphenyl, phenanthryl, and anthracyl. If the aryl is specified as "monocyclic aryl," if refers to an aromatic group containing only a single ring, i.e., not a fused ring.

Heteroaryl is aryl containing at least one (e.g., 1-3) heteroatom such as nitrogen, oxygen, or sulfur and can contain fused rings. Some examples of heteroaryl are pyridyl, furanyl, pyrrolyl, thienyl, thiazolyl, oxazolyl, imidazolyl, indolyl, benzofuranyl, and benzthiazolyl.

Halogen or halo may be fluoro, chloro, bromo or iodo.

The hydrolyzable moiety can be methyl, t-butyl, benzyl, p-methoxybenzyl, p-nitrobenzyl, allyl, trityl, methoxymethyl, 2-methoxypropyl, methoxyethoxymethyl, ethoxyethyl, tetrahydropyranyl, tetrahydrothiopyranyl, and trialkylsilyl ethers such as trimethylsilyl ether, triethylsilyl ether, dimethylarylsilyl ether, triisopropylsilyl ether and t-butyldimethylsilyl ether; esters such as benzoyl, acetyl, phenylacetyl, formyl, mono-, di-, and trihaloacetyl such as chloroacetyl, dichloroacetyl, trichloroacetyl, trifluoroacetyl; and carbonates including but not limited to alkyl carbonates having from one to six carbon atoms such as methyl, ethyl, n-propyl, isopropyl, n-butyl, t-butyl; isobutyl, and n-pentyl; alkyl carbonates having from one to six carbon atoms and substituted with one or more halogen atoms such as 2,2,2-trichloroethoxymethyl and 2,2,2-trichloro-ethyl; alkenyl carbonates having from two to six carbon atoms such as vinyl and allyl; cycloalkyl carbonates having from three to six carbon atoms such as cyclopropyl, cyclobutyl, cyclopentyl and cyclohexyl; and phenyl or benzyl carbonates optionally substituted on the ring with one or more $C_{1-6}$ alkoxy, or nitro.

Pharmaceutical compositions can include derivative of plumbagin. More particularly, such compounds can be formulated as pharmaceutical compositions using standard pharmaceutically acceptable carriers, fillers, solubilizing agents and stabilizers known to those skilled in the art. For example, a pharmaceutical composition including a derivative of plumbagin, or a salt, analog, derivative, or modification thereof, as described herein, is used to administer the appropriate compound to a subject.

A derivative of plumbagin can be useful for treating cancer in a subject by administering to a subject in need thereof of a therapeutically acceptable amount of a compound, for example, of formula (I) or formula (II), or a pharmaceutical composition comprising a therapeutically effective amount of a compound of, for example, formula (I) or formula (II), and a pharmaceutically-acceptable carrier. The cancer can be breast cancer, leukemia, lung cancer, colon cancer, pancreatic cancer, CNS cancer, melanoma, ovarian cancer, cervical cancer, renal cancer, prostate cancer, carcinoma or adenocarcinoma. In some embodiments, the cancer, carcinoma or adenocarcinoma is metastatic, advanced and/or late-stage (e.g., stage III or later).

The dose of a derivative of plumbagin administered to a subject can be less than 10 μg, less than 25 μg, less than 50 μg, less than 75 μg, less than 0.10 mg, less than 0.25 mg, less than 0.5 mg, less than 1 mg, less than 2.5 mg, less than 5 mg, less than 10 mg, less than 15 mg, less than 20 mg, less than 50 mg, less than 75 mg, less than 100 mg, or less than 500 mg.

Administering can include administering by topical, enteral, parenteral, transdermal, transmucosal, inhalational, intracisternal, epidural, intravaginal, intravenous, intramuscular, subcutaneous, intradermal or intravitreal administration.

A compound described herein can be formulated into dosage forms for other routes of administration utilizing conventional methods. For example, it can be formulated in a capsule, a gel seal, or a tablet for oral administration. Capsules may contain any standard pharmaceutically acceptable materials such as gelatin or cellulose. Tablets may be formulated in accordance with conventional procedures by compressing mixtures of a compound described herein with a solid carrier and a lubricant. Examples of solid carriers include starch and sugar bentonite. Compounds of this invention can also be administered in a form of a hard shell tablet or a capsule containing a binder, e.g., lactose or mannitol, a conventional filler, and a tableting agent.

The compounds can be prepared by ordinary synthetic organic techniques, for example, as described in J. March, Advanced Organic Chemistry, which is incorporated by reference in its entirety.

The activities of a compound described herein can be evaluated by methods known in the art, e.g., MTT (3-[4,5-dimehtythiazol-2-yl]-2,5-diphenyltetrazolium bromide) assay, APOPercentage, clonogenic assay, ATP assay, or Extreme Drug Resistance (EDR) assay. See Freuhauf, J. P. and Manetta, A., Chemosensitivity Testing in Gynecologic Malignancies and Breast Cancer 19, 39-52 (1994), which is incorporated by reference in its entirety. The results are then plotted to generate drug response curves, which allow $IC_{50}$ values (the concentration of a compound required to inhibit 50% of the population of the treated cells) to be determined. The amount of the compound, or an active salt or derivative thereof, required for use in treatment can vary not only with the particular salt selected but also with the route of administration, the nature of the condition being treated and the age and condition of the patient and can be ultimately at the discretion of the attendant physician or clinician. In general, however, a dose can be in the range of from about 0.01 to about 10 mg/kg of body weight per day.

Other anti-cancer assays are well-known in the art, including in vitro exposure of agents to tumor cells and in vivo antitumor assays in rodent models and rarely, in larger animals.

The disclosed method can include a kit comprising a derivative of plumbagin and instructional material which can describe administering the compound or a composition comprising the compound to a cell or a subject.

A pharmaceutical composition can include the derivative of plumbagin, alone or in combination with another pharmaceutically active ingredient in which case the derivative of plumbagin can act as a pharmaceutical adjuvant. The composition can include one or more other pharmaceutical adjuvants or excipients.

In accordance with the disclosed methods, as described above or as discussed in the Examples below, there can be employed conventional chemical, cellular, histochemical, biochemical, molecular biology, microbiology, and in vivo techniques which are known to those of skill in the art. Such techniques are explained fully in the literature.

EXAMPLES

Plumbagin and its five derivatives (A, B, C, D, and E) were evaluated for their cytotoxicity potential in four human cancer and one normal cell lines, where derivative 'A' was acetyl plumbagin. FIGS. 1A-1E show the results of the cytotoxicity screening in time-course experiment (12, 24, 36 and 48 hr) using MTT assay. Derivative 'A' has selective apoptotic activity like plumbagin against MCF-7 cells; however, normal fibroblasts are relatively unaffected. Derivative 'A' also displayed negligible hepatotoxicity (data based on HepG2 cell line). Based on these results, acyl derivative of plumbagin, derivative 'A' (acetyl plumbagin) was chosen for further investigations of its apoptosis inducing potential in breast cancer cell lines, MCF-7 (estrogen receptor positive) and BT20 (estrogen receptor negative), along with normal fibroblasts (BJ) by using APOPercentage dye uptake assay (12 and 24 hr) and caspase-3/7 assay at various concentrations in time-course (1, 2, 4, 8 and 16 hr) experiments.

MTT Assay

The cytotoxicity of plumbagin and derivative 'A' was estimated by MTT assay. Cells were plated in a 384-well culture plates (2000 cells per well in 20 μl of media) for 24 h and cells were treated with various concentrations (0, 1.0, 5.0, 10.0, 20.0, 40.0, 80.0 and 100.0 μM) for 12 hr, 24 hr, 36 hr and 48 hr. Following desired incubation time, 5 μl of sterile 5 mg/ml MTT (3-(4,5-Dimethylthiazol-z-yl)-2,5diphenyltetrazolium bromide) (Sigma) dissolved in PBS was added to each well and the cells were incubated for another 4 hr followed by the addition of 30 μl of solubilisation solution (10% SDS, 10 mM HCl) and incubation for 16 hr at 37° C. The OD of each well at 595 nm was determined using a microtiter plate reader (BMG Pherastar).

MTT assay results showed that the derivative 'A' has cytotoxicity comparative to plumbagin in MCF-7 (human breast cancer cell line) at 10 μM concentration after 12 hr of treatment. However, the toxicity of the derivative 'A' against BJ cell line (human normal fibroblast cells) at 10 μM is almost nil at 12 hr and ~20 times less at 24 hr as compared to plumbagin at the same concentration. Even after 36 hr of induction, the toxicity of derivative 'A' is ~4.5 folds less than Plumbagin in BJ cell line.

Figure 2:
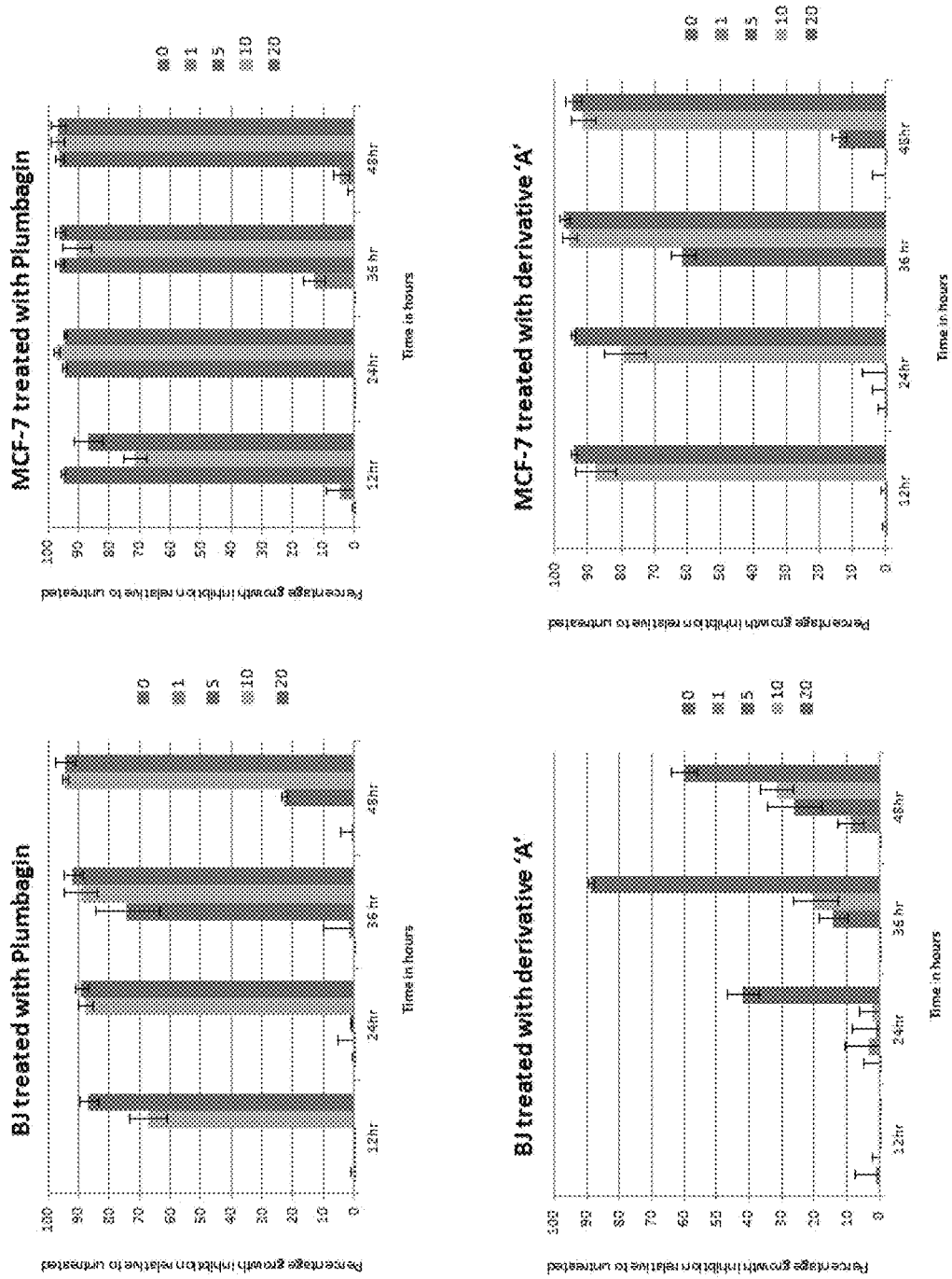
FIG. 2 is a graph depicting the effects of different concentrations (0-20 µM) of plumbagin and its derivative 'A' on cell proliferation of MCF-7 and BJ cell lines. Graphs represent cell growth inhibition in cell lines.

The detailed graphs comparing the growth inhibiting properties of plumbagin and its derivative 'A' are presented in FIG. 2. The graphs clearly demonstrate that Plumbagin inhibits metabolic activity of 90% cancer cells at 5 μM within 12 hr of treatment and approximately 70% normal cells 'BJ'at 10 μM within 12 hr of treatment. But the activity of derivative 'A' is 90% at 10 μM after 12 hr of treatment in cancer cells whereas normal cells 'BJ' are inhibited only 20% at 20 μM even after 36 hr of treatment.

APOPercentage Assay

MTT is a pre-screening method of measuring the metabolic growth inhibition potential of a compound, showing that plumbagin and its derivate are cytotoxic to cancer cells in culture, but it does not specify the mode of cell death. To further test if the cancer cells in present investigation are dying via apoptosis, a dye inclusion assay called APOPercentage was performed. APOPercentage™ is a dye-uptake assay that detects apoptotic cells during phospholipid phosphatidylserine (PS) trans-membrane movement. It has been established previously that APOPercentage™ can be used to detect early stages of apoptosis as efficiently as other technologies like Annexin V.

The cells were plated in 96 well plates at a density of $5 \times 10^3$ cells per well in triplicate in 90 μl of media. The cells were treated with 10 μl of desired concentration of plumbagin and derivative 'A' in DMEM media. The cells were incubated at 37° C. for 12 hr and 24 hr in different plates. 5 mM $H_2O_2$ was treated for 30 minutes to 1 hour as a positive control. The cells were stained with APOPercentage dye as per instructions from the vendor (Biocolor, UK). The cells were photographed with Nikon TS100 microscope. The OD was measured at 550 nm absorbance using BMG Pherastar and percentage of cells taking up APOPercentage dye was calculated.

Figure 3A:
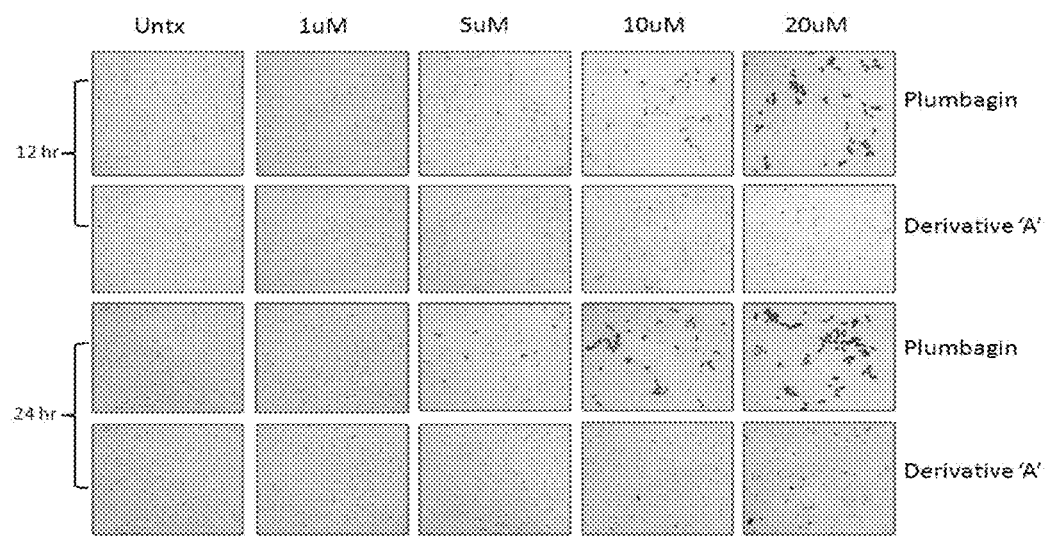
FIGS. 3A and 3B are photographs of cells stained with APOPercentage dye after treatment with different concentrations (0-20 µM) of plumbagin and derivative 'A'.
Figure 3B:
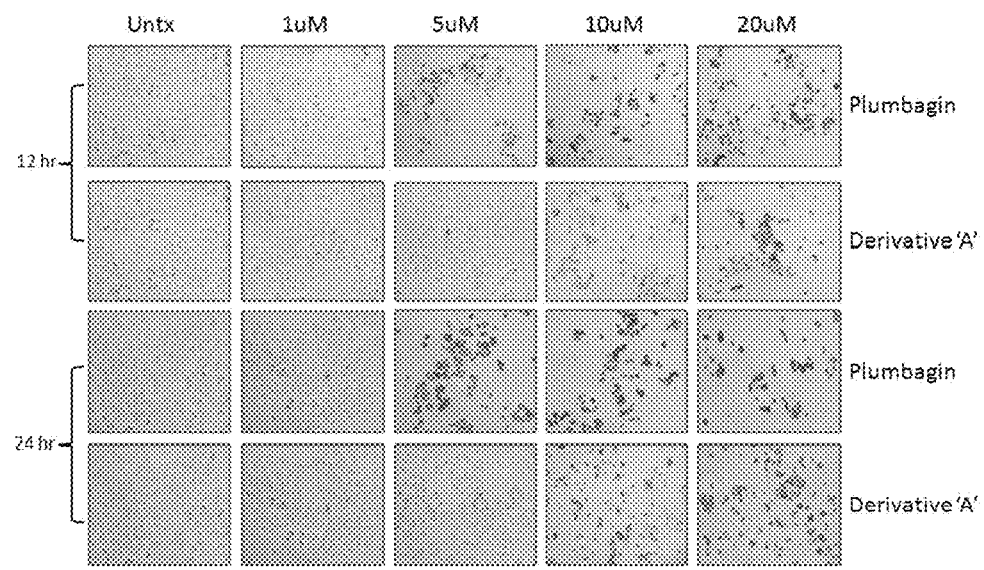
Figure 4A:
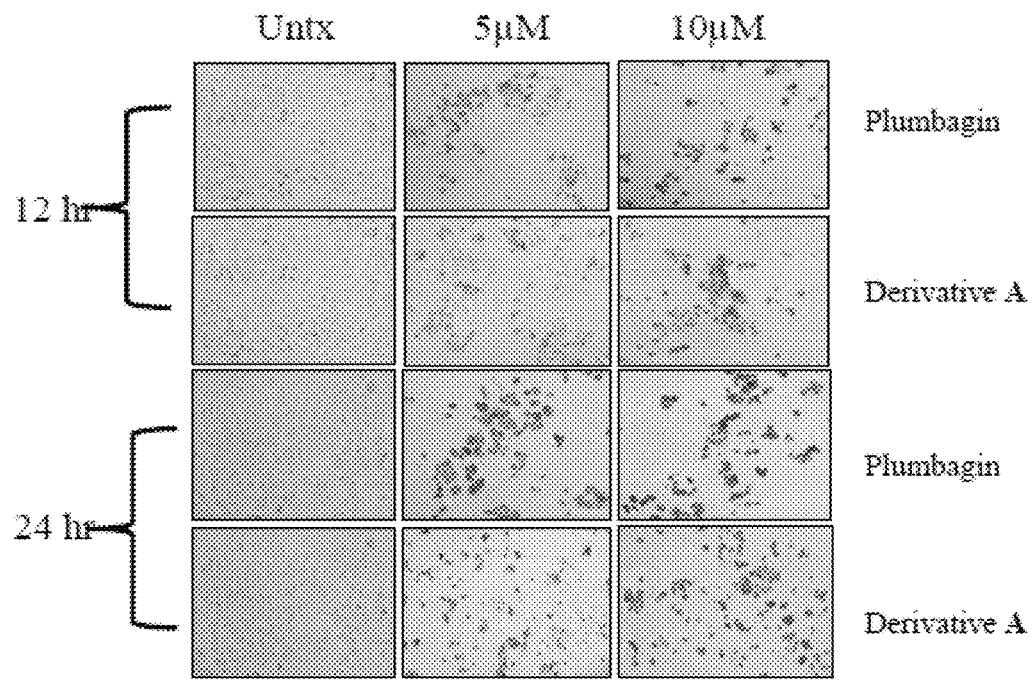
FIG. 4A is a photograph of cells stained with APOPercentage dye after treatment with different concentrations (0, 5 or 10 µM) of plumbagin and derivative 'A'.
Figure 4B:
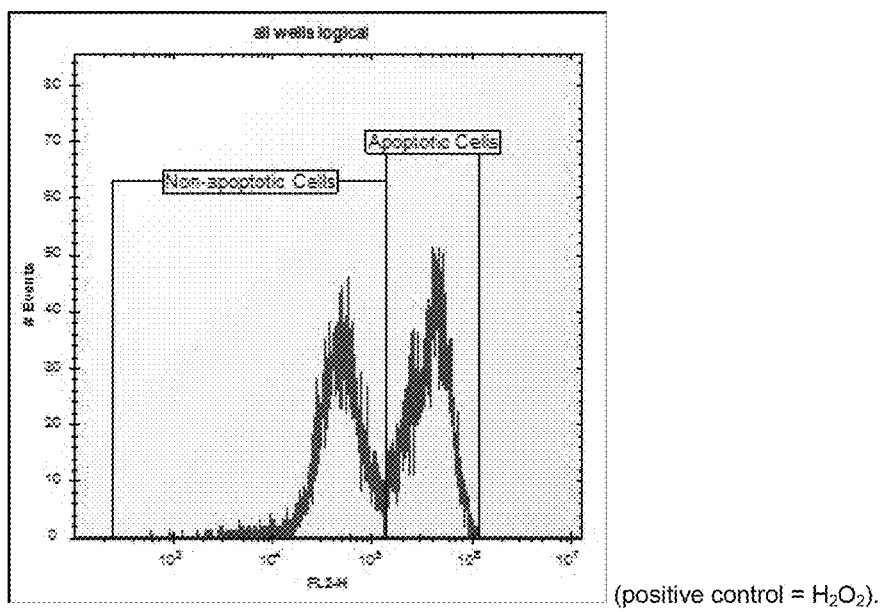
FIG. 4B is a graph of APOPercentage dye uptake measured by flow cytometry.
Figure 4C:
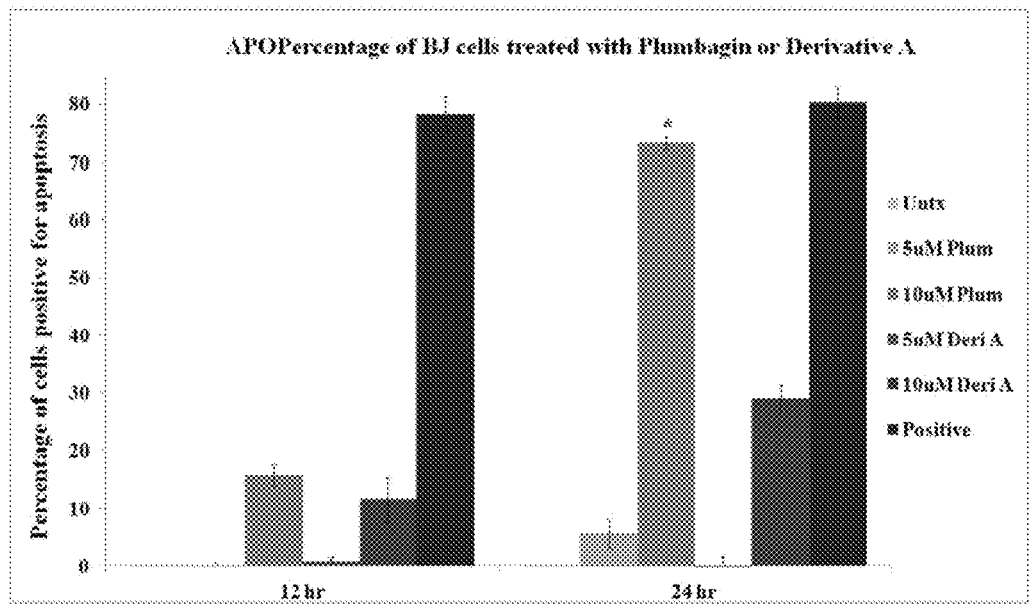
FIGS. 4C-4E are a series of graphs depicting the percentage of apoptotic cells (based on dye uptake) at 12 and 24 hr in BJ cells (FIG. 4C), MCF-7 cells (FIG. 4D), and BT20 cells (FIG. 4E).
Figure 4D:
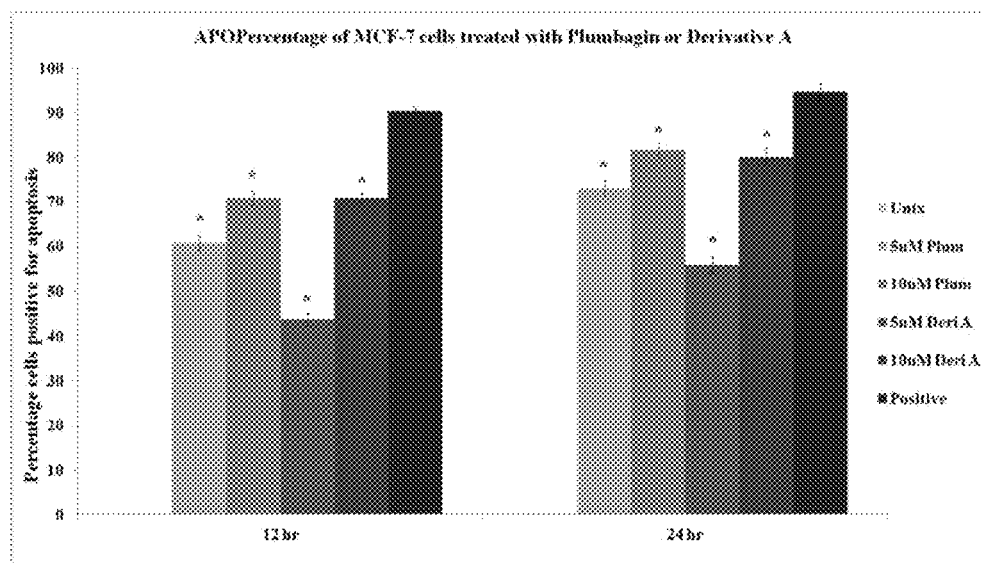
Figure 4E:
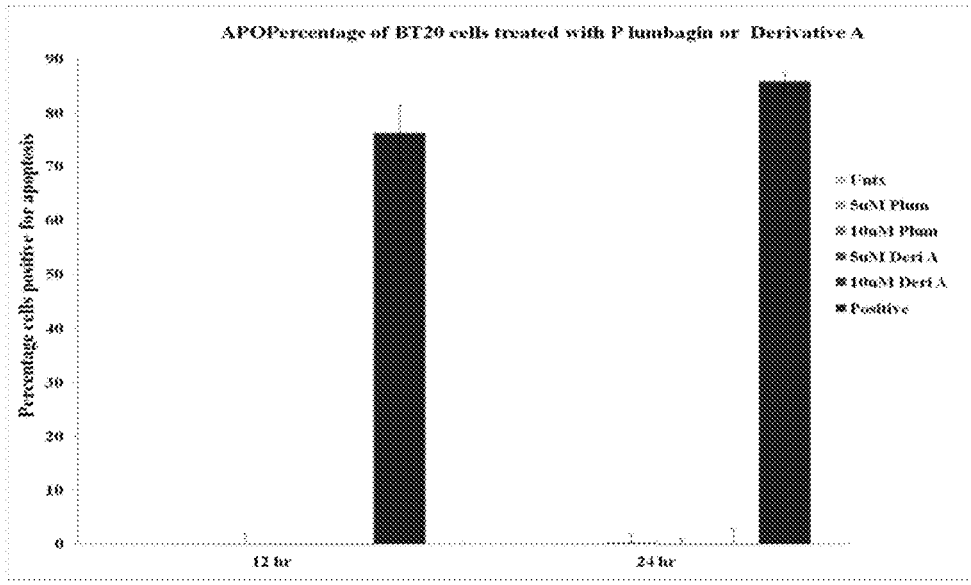

The results of the APOPercentage assay show that the predominant mode of cell death by plumbagin and its derivative is via apoptosis. The APOPercentage assay show that the cells dying via apoptosis take up pink stain and this represent a hallmark of membrane flipping in cells undergoing apoptosis. FIGS. 3A and 3B show the pictures of the APOPercentage assay of untreated, treated with test compounds and positive control treated cells performed at time intervals of 12 hr and 24 hr to capture this particular stage of apoptotic cells. FIGS. 4A-4E show plumbagin- and derivative A- dependent induction of apoptosis in BJ, MCF-7 and BT20 cells. APOPercentage results show the cytotoxicity trends of derivative 'A' and plumbagin for cancer and normal cells.

Caspase-3/7 Assays

Figure 5A:
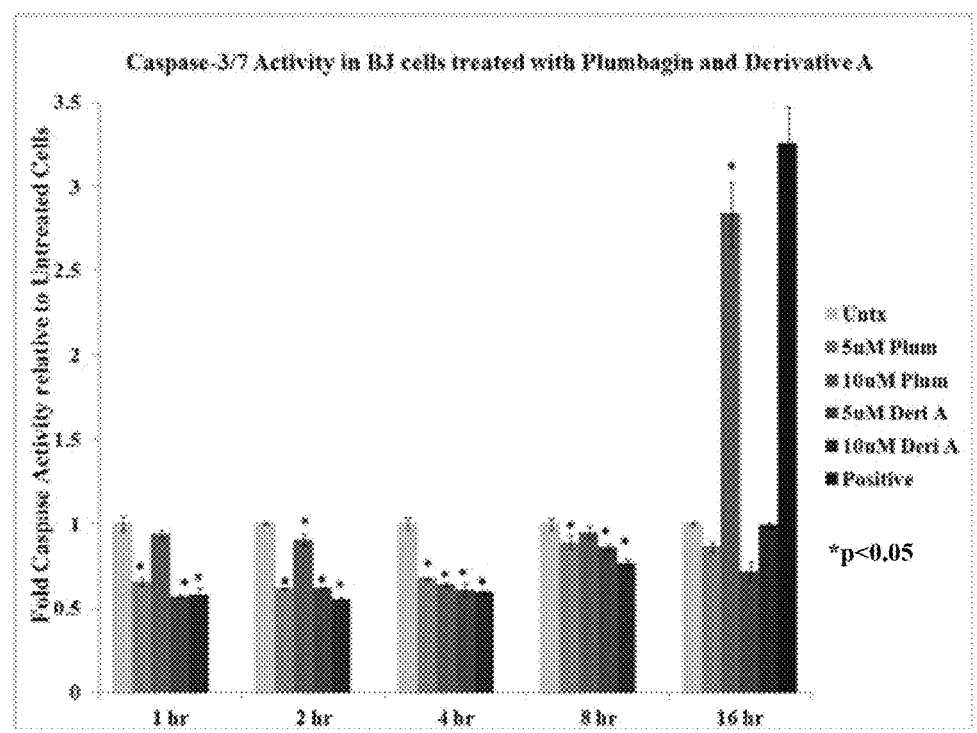
FIGS. 5A-5C are a series of graphs depicting the effect of plumbagin and derivative 'A' on caspases-3/7 activity of BJ (FIG. 5A), MCF-7 (FIG. 5B) and BT20 (FIG. 5C) cells.
Figure 5B:
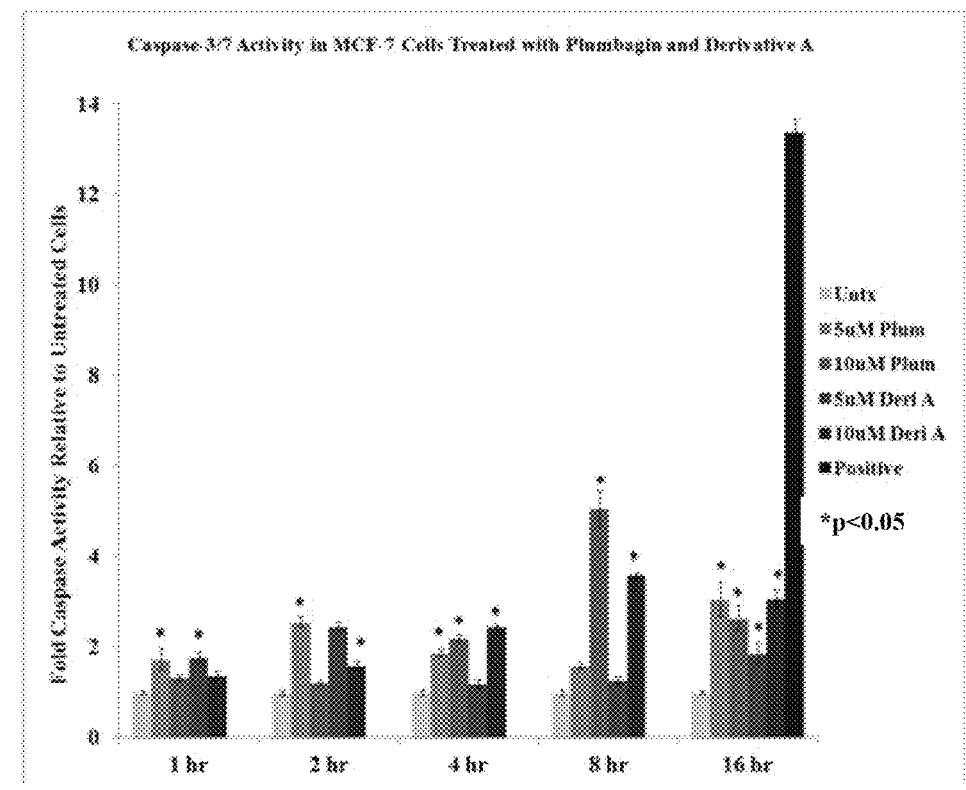
Figure 5C:
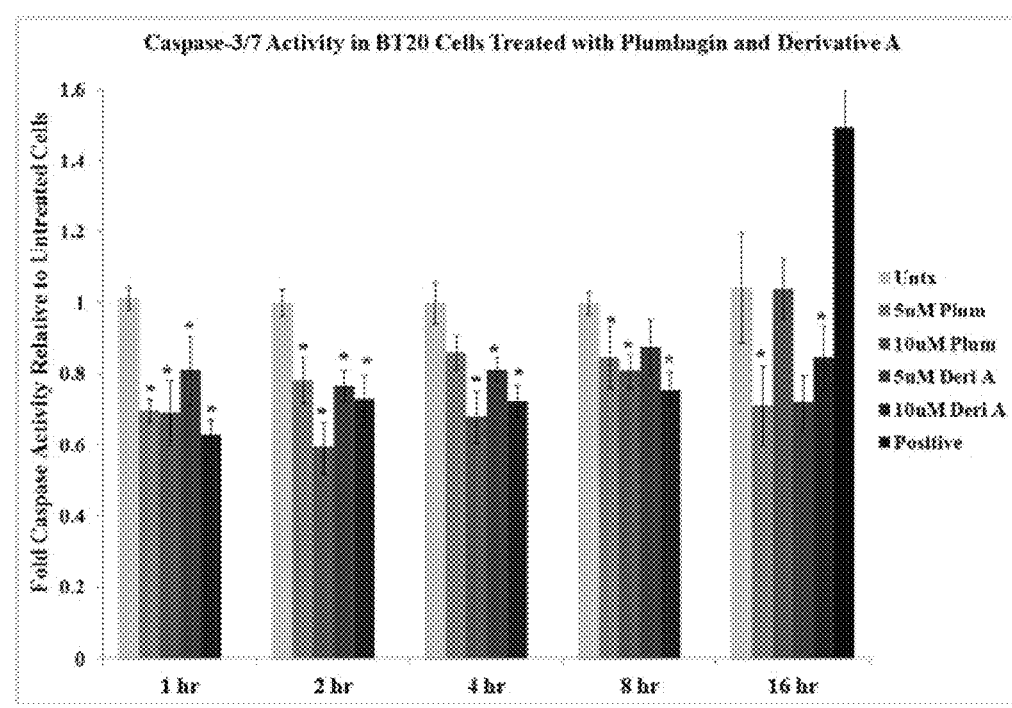

FIGS. 5A-5C show plumbagin and derivative 'A'-dependent induction of caspases-3/7 activity in BJ, MCF-7 and BT20 cells. Cells were incubated with 5 and 10 μM of plumbagin (plum) and derivative 'A' (Deni A) for 1, 2, 4, 8 or 16 hr. Fold changes in caspases-3/7 activity after treatment with plumbagin and derivative 'A' in a timecourse experiment in BJ cells (FIG. 5A), MCF-7 cells (FIG. 5B), and BT20 cells (FIG. 5C) are shown. Docetaxel (200 nM) is used as positive control. Data are mean±S.D. (n=4), *p<0.05 significant difference to untreated (Untx) control.

These results demonstrate that derivative 'A' has anticancer potential and it induces growth inhibition and apoptosis in MCF-7 cells but normal cells 'BF'remain relatively unaffected by treatment of derivative 'A' even up to 20 μM concentration after treatment for 12 hr. Even after 24 hr, 20% of normal cells undergo apoptosis while 100% of cancer cells are undergoing apoptosis. A concentration of 10 μM of derivative 'A' is safe for normal cells even after treatment for 24 hr while the same concentration induces apoptosis in about 50% of cancer cells. Plumbagin induces apoptosis in cancer cells even at lower concentration of 5 μM within 24 hr of treatment but it also induces apoptosis in normal cells 'BF'at lower concentration than its derivative 'A'. The results presented here show that derivative 'A' has significantly low toxicity for normal cells even at higher concentrations as compared to plumbagin. Derivative 'A' has a specific activity for human breast cancer cells.

To further support evidence for low toxicity of the derivative 'A', the $IC_{50}$ values of the derivative 'A' against HepG2 (Hepatocellular carcinoma) cell line were calculated. HepG2 has been used as an in vitro model to study the hepatotoxicity effects of drugs. Several published studies have demonstrated the use of this cell line as an indicator of the hepatotoxicity induced by a drug (Van Summeren et al., TOXICOLOGICAL SCIENCES 121(2), 431-433 (2011), which is incorporated by reference in its entirety). The $IC_{50}$ values of the plumbagin and derivative 'A' were 10.22 μM and 41.25 μM respectively after 24 hr of treatment. This shows that derivative 'A' is less hepatotoxic to liver as compared to plumbagin.

In Vivo Experiments

In vivo experiments in nude mice aiming at efficacy testing and basic toxicology profiling of derivative 'A' using ALT (alanine aminotransferase) and AST (aspartate aminotransferase) markers were performed.

Methods

1. Compound Preparation

Vehicle: Add PEG400 into the 0.9% (weight/volume) saline/NaCl solution, to generate a final concentration of 25% PEG400. The solution was aliquoted into small tubes, and stored in −20° C. The injection volume was about 200 μl/20 g nude mouse weight.

Derivative 'A': The derivative 'A' was dissolved in PEG400 first, then diluted in 0.9% (weight/volume) saline/NaCl solution, to generate a final concentration of 25% PEG400. The drug solution was aliquoted into small tubes, and stored in −20° C. The injection volume was about 200 ul/20 g nude mouse weight.

Plumbagin: The plumbagin was dissolved in PEG400 first, then diluted in 0.9% (weight/volume) saline/NaCl solution, to generate a final concentration of 25% PEG400. The drug solution was aliquoted into small tubes, and stored in −20° C. The injection volume was about 200 μl/20 g nude mouse weight.

2 Implantation

Amplified and implanted (S.C.) the cancer cells (MCF-7) into 4 nude mice with $1.0 \times 10^7$ cells in 0.1 ml PBS plus matrigel (1:1) /mouse, when tumors reach 300-500 $mm^3$, the tumor masses were harvested, cut into small pieces of approximately 1-2 $mm^3$, and then surgically implanted into the 42 new nude mice for model set up (eventually 30 tumor-bearing mice are selected).

3. Groups and Dosage

When the tumor size reached a volume of 150 (150-220) $mm^3$, the tumor-bearing nude mice derived from MCF-7 cells were randomly assigned into 3 groups (10 mice/group): Group 1 was served as vehicle group (25% PEG400, 200 μl/20 g mouse, i.p, qd for 21 days and 25% PEG400, 400 μl/20g mouse, i.p, qd for 13 days), group 2 was administrated with derivative 'A' (5 mg/kg for 21 days and 10 mg/kg for 13 days, i.p, qd), group 3 was administrated with plumbagin (2 mg/kg for 21 days, i.p, qd). The administration period lasted for 3 weeks and 5 weeks. The detailed sacrificing schedule is described in section 5.

4. Physical Examinations

If abnormal appearance and behavior or signs of morbidity and/or mortality was seen through the cage side observation, the veterinarian would be notified and proper physical examination and/or necropsy would be performed. The food consumption in each group would be recorded. Frequency: daily just after the cell inoculation and twice a day thereafter starting on first dosing.

5. Measurement

The tumor volume was measured every other day with calipers, and the body weight was measured immediately before measuring the tumor volume throughout the whole study. If the body weight loss is approaching 20%, stop dosing or decreased dosage will be carried out.

6. Terminal Procedures and Necropsy a. Early Death/Unscheduled Necropsy

If a mouse dies on study, the time of death will be estimated as closely as possible and recorded, and the mouse will be necropsied as soon as possible. If the necropsy cannot be performed immediately, the mouse was refrigerated (not frozen) to minimize tissue autolysis and necropsied no later than 12 hours following death. If a mouse appears in poor condition or in extremes, it may be euthanized (as described below) per the Testing Facility's policies on humane care of animals. If the tumor burden larger than 2000 $mm^3$ or the body weight loss greater than 30% baseline body weight, the mice will be euthanized. If the weight dropped significantly, or relative body weight difference of treated vs vehicle is large, the data was viewed with a caveat. All unscheduled-necropsy mice will be necropsied immediately, or, if this cannot be performed, the mouse will be refrigerated to minimize autolysis and necropsied no later than 12 hours after death.

b. Scheduled Necropsy

At the end of the experiment (the 22nd day after initiating drug treatment), the blood from some tumor-bearing mice per group (4 mice from the group 1, 5 mice from the group 2, 4 mice from the group 3) were collected by cardiac puncture, and the mice were sacrificed by cervical dislocation while under deep anesthesia. The other tumor-bearing mice from each group (5 mice from the group 1, 5 mice from the group 2) were sacrificed after another 13 days treatment (the 35th day after initiating drug treatment), the blood was collected while sacrificing the mice. The tumor samples were harvested, weighed, cut into small pieces and snap frozen in liquid nitrogen for RNA extraction. The liver were harvested and fixed in 10% NBF, and embedded in paraffin for histology analysis.

7. Endpoints a. Serum Collection and Analysis

Blood were collected from all animals by terminal bleed for subsequent serum preparation, and serum was prepared at the end of the study for each animal. Serum samples were frozen in microcentrifuge tube at −80° C. To test the liver toxicity of the two compounds, biochemical dictators (ALT, AST) were analyzed in all the serum samples no more than 3 days after collection. The excess serum samples would be sent to client.

b. Tumor Volume and Tumor Weight

Tumor sizes were measured every other day in two dimensions using a caliper, and the volume were expressed in $mm^3$ using the formula: $V = \frac{1}{2} \times a \times b^2$ where a and b are the long and short diameters of the tumor, respectively.

The tumor mass were weighed and photographed at the end of the experiment after harvested. The tumor mass were cut into small pieces and snap frozen in liquid nitrogen for RNA extraction.

c. Tumor Pieces RNA Extraction

The tumor pieces in liquid nitrogen were used for the RNA extraction, the extracted RNA was used for further analysis.

d. Liver Tissue Harvest and H&E Staining

To test the liver toxicity of the two compounds, livers were harvested from all animals while sacrificing the animals. One piece of the liver was fixed in 10% NBF, and embeded in paraffin for pathology analysis, 1 paraffin block was prepared from each liver sample, 2 slides were used for H&E staining.

e. Inhibition Rate

Inhibition rate (%)=(average tumor volume of control group-average cancer volume of test group)/average tumor volume of control group ×100%

8. Statistical Analysis

Differences between two groups of tumor volume were analyzed by SPSS 16.0 with one-way ANOVA statistic test. $P<0.05$ will be considered statistically significant.

Results

1. Comparison of the Tumor Inhibition Potential of Derivative 'A' and Plumbagin

Figure 6B:
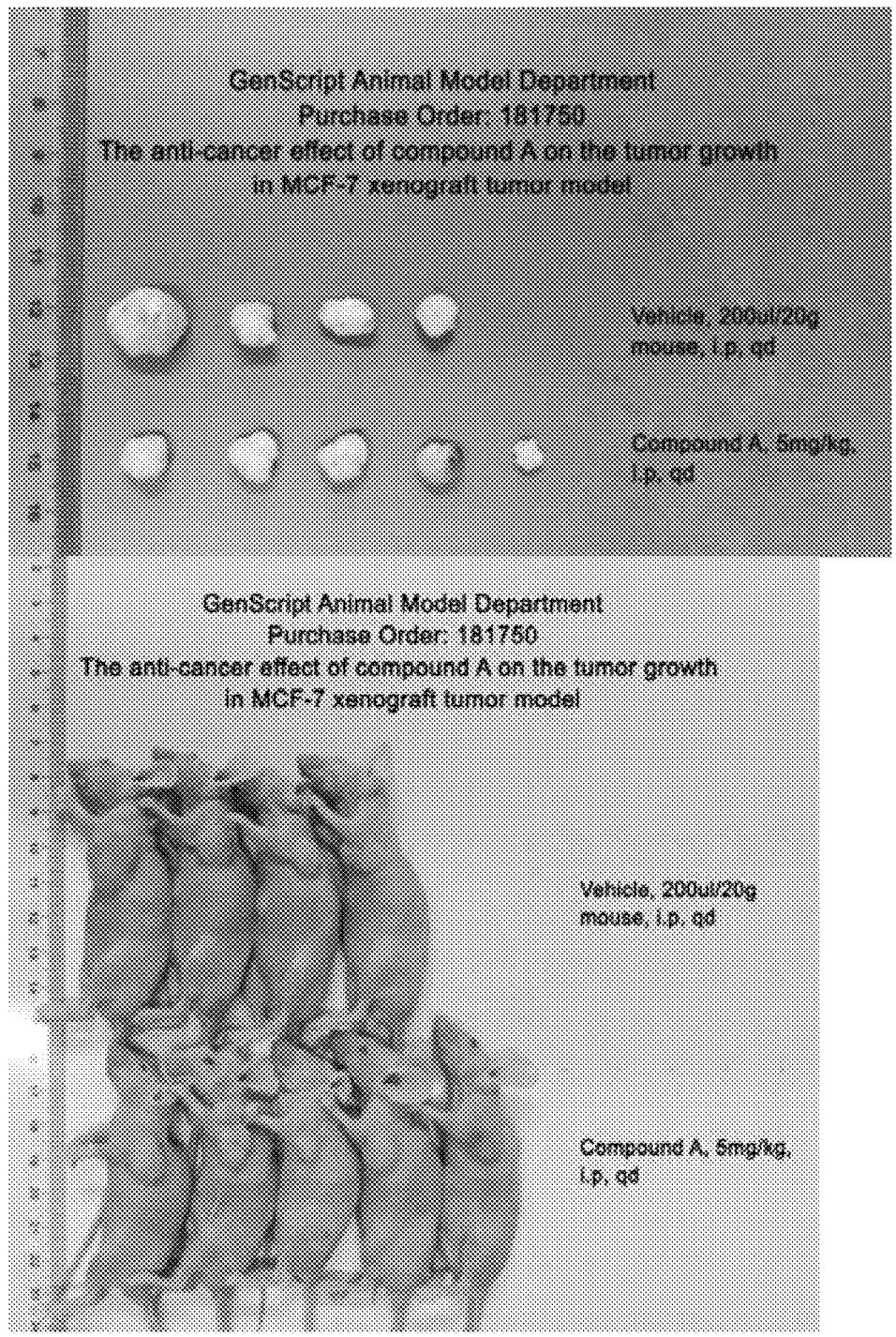

FIGS. 6A-6B shows the sizes of the tumors obtained from different group of mice. The tumor size is smaller (on average) in group of mice treated with derivative 'A'.

Figure 7A:
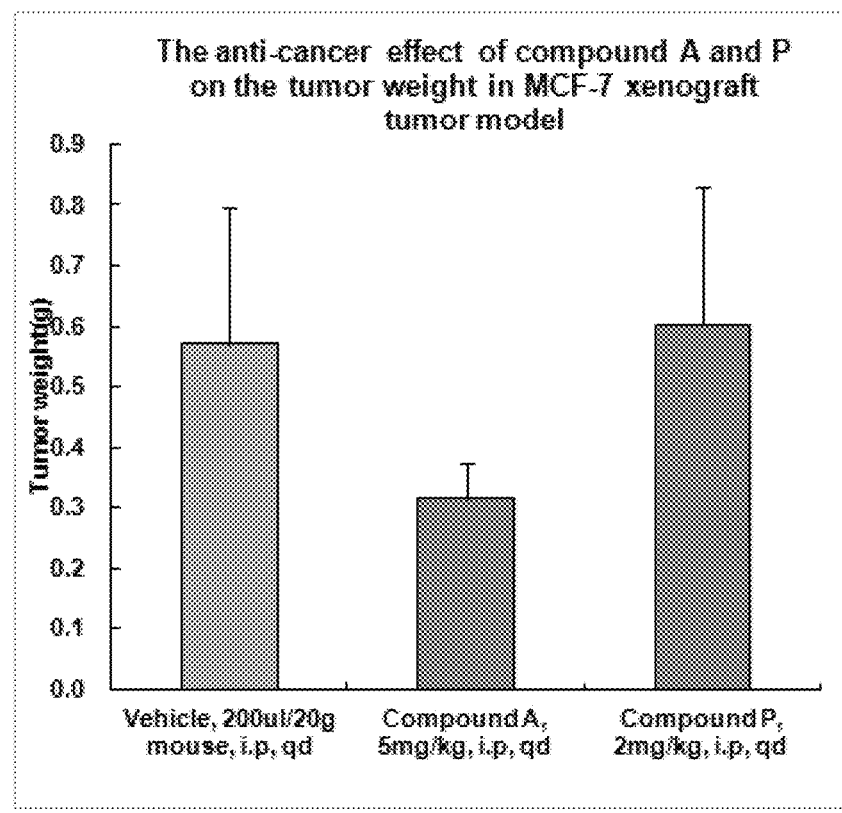
FIGS. 7A-7B are graphs depicting the comparison of the inhibition rates of vehicle, plumbagin and derivative 'A'.
Figure 7B:
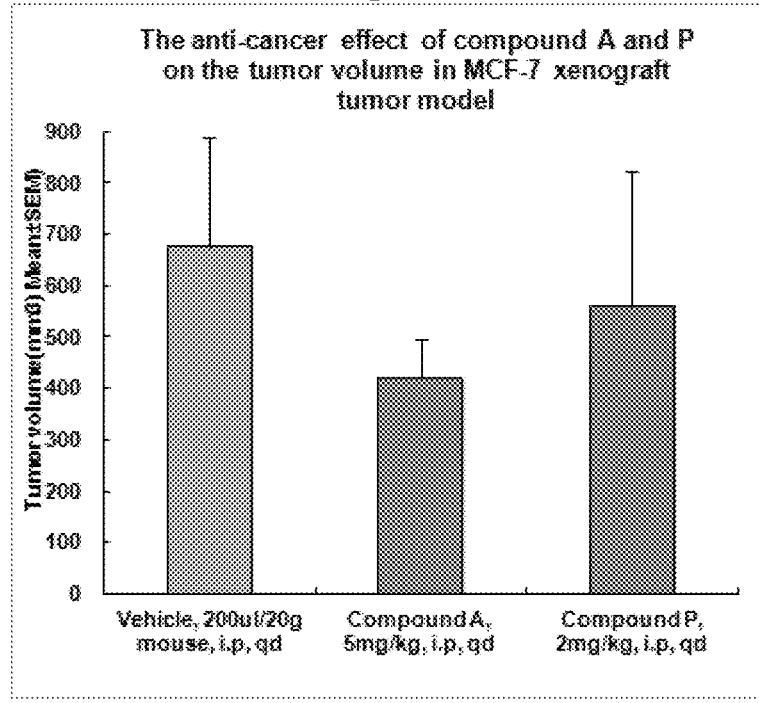

Table 1 and FIG. 7A represent the data and results comparing the tumor inhibition rates of derivative 'A' and plumbagin based on tumor weight (after autopsy). Similarly, Table 2 and FIG. 7B represent the data and results comparing the tumor inhibition rates of derivative 'A' and plumbagin based on tumor volume (measurements taken on live animals using calipers). The tumor volume measurements can be skewed because the tumor depth cannot be measured externally.

Figures 9A, 9B:
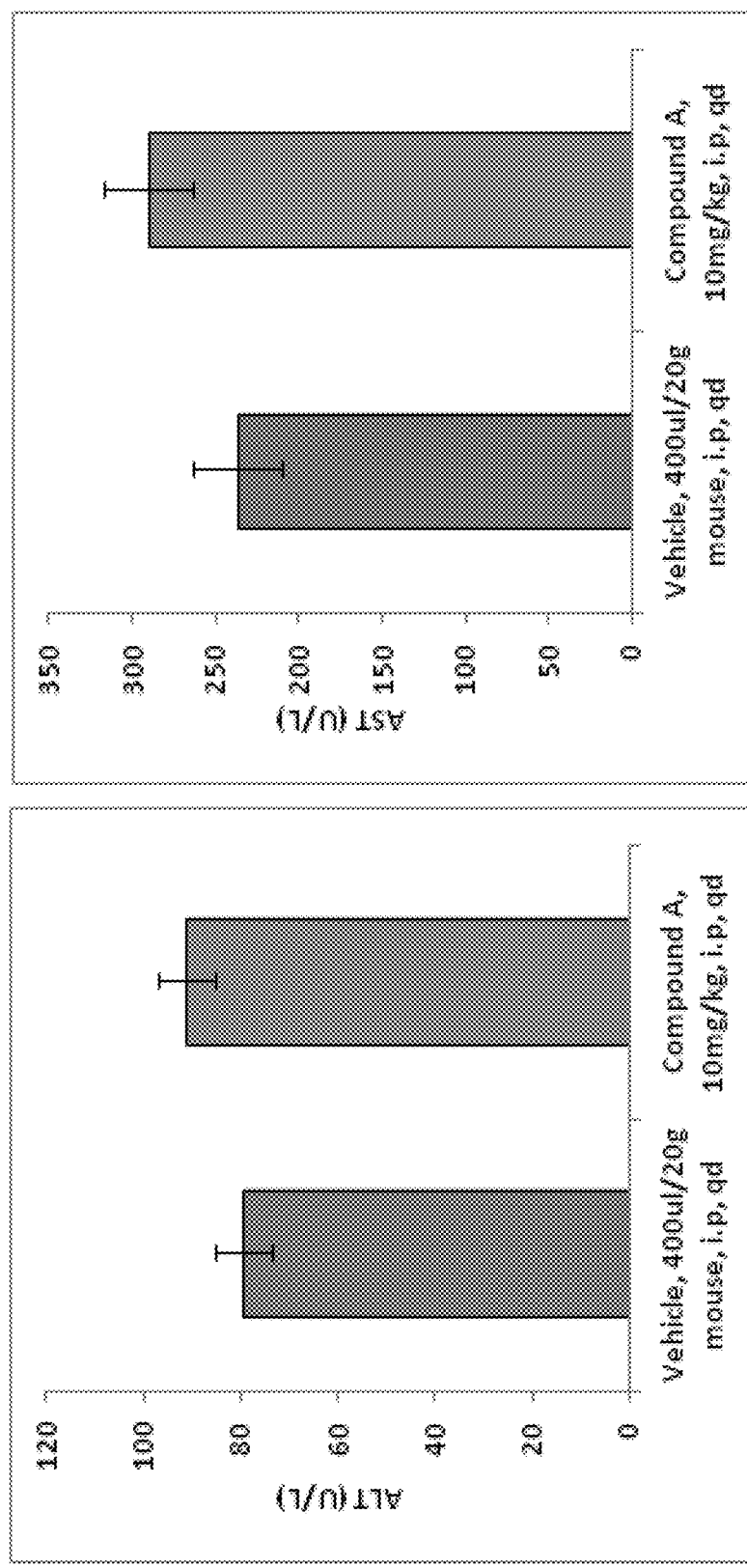
FIGS. 9A-9B are graphs depicting the comparison of ALT (FIG. 9A) and AST (FIG. 9B) of mice groups after treating the mice with double dose for additional 13 days.

2. Comparison of the Liver Toxicity Profiles of Compounds A and P a. Serum Collection and Analysis The serum was collected as explained above in methods and was used to assess the activity of ALT (alanine aminotransferase) and AST (aspartate aminotransferase). After 21 days of treatment, 5 mice were available both in vehicle and derivative 'A' groups (FIGS. 8A-8B). In order to measure the toxic effects of derivative 'A' at higher doses, remaining mice were treated with a dose of 10 mg/kg along with double dose of the vehicle (FIGS. 9A-9B).

These graphs show increased values of ALT and AST with increasing dose of derivative 'A', but note that the data of one mouse was an outlier in terms of values of ALT and AST (see Table 3 below, yellow highlight):

TABLE 1

Tumor weight at autopsy

| | Group | | | | | | | | | Tumor inhibition rate |
| --- | --- | --- | --- | --- | --- | --- | --- | --- | --- | --- |
| | 1 | 2 | 3 | 4 | 5 | AV | SD | SEM | P value | (C − T)/C × 100% |
| Vehicle, 200 ul/20 g mouse, i.p, qd | 1.3177 | 0.3823 | 0.3225 | 0.2633 | | 0.5715 | 0.500 | 0.224 | | |
| Compound A, 5 mg/kg, i.p, qd*21 days | 0.3930 | 0.3862 | 0.3802 | 0.3290 | 0.0843 | 0.3145 | 0.131 | 0.059 | 0.29965 | 44.96% |
| Compound P, 2 mg/kg, i.p, qd*21 days | 1.3530 | 0.4301 | 0.3675 | 0.2574 | | 0.6020 | 0.506 | 0.226 | 0.93432 | −5.35% |

TABLE 2

Tumor volume measured externally

| | Group | | | | | | | | | Tumor inhibition rate |
| --- | --- | --- | --- | --- | --- | --- | --- | --- | --- | --- |
| | 1 | 2 | 3 | 4 | 5 | AV | SD | SEM | P value | (C − T)/C × 100% |
| Vehicle, 200 ul/20 g mouse, i.p, qd | 1373.2 | 501.9 | 358.7 | 368.2 | | 675.5 | 478.5 | 214.0 | | |
| Compound A, 5 mg/kg, i.p, qd*21 days | 493.1 | 595.4 | 151.4 | 486.0 | 378.5 | 420.9 | 169.1 | 75.6 | 0.29893 | 37.69% |
| Compound P, 2 mg/kg, i.p, qd*21 days | 1441.7 | 260.9 | 234.5 | 303.8 | | 560.2 | 588.3 | 263.1 | 0.77139 | 17.07% |

Above results show that the derivative 'A' at 5 mg/kg concentration inhibited tumor growth by approximately 45% as compared to the vehicle and plumbagin (2 mg/kg). The use of different treatment concentrations (dosages) of derivative 'A' and plumbagin was due to the high toxicity of plumbagin at 5 mg/kg dose (8 mice died due to toxicity in first few days). The 2 mg/kg dose was thought to be well tolerated by mice (a separate treatment regimen was performed by Genscript to check the drug tolerance, where doses of 1 mg/kg, 2 mg/kg and 3 mg/kg of plumbagin were administered to mice and based on their response in terms of body weight loss) and it was decided that 2 mg/kg dose can be used for further treatments.

TABLE 3

ALT and AST values measured in individual mouse in vehicle and derivative 'A' treated groups

| ALT | AST |
| --- | --- |
| Vehicle, 400 ul/20 g mouse, i.p, qd | |
| 41 | 216 |
| 48 | 211 |
| 96 | 205 |
| 101 | 328 |
| 110 | 223 |

TABLE 3-continued

ALT and AST values measured in individual mouse in
vehicle and derivative 'A' treated groups

| ALT | AST |
|---|---|
| Compound A, 10 mg/kg, i.p, qd | |
| 51 | 209 |
| 54 | 297 |
| 55 | 230 |
| 88 | 199 |
| 207 | 514 |

Figure 10:
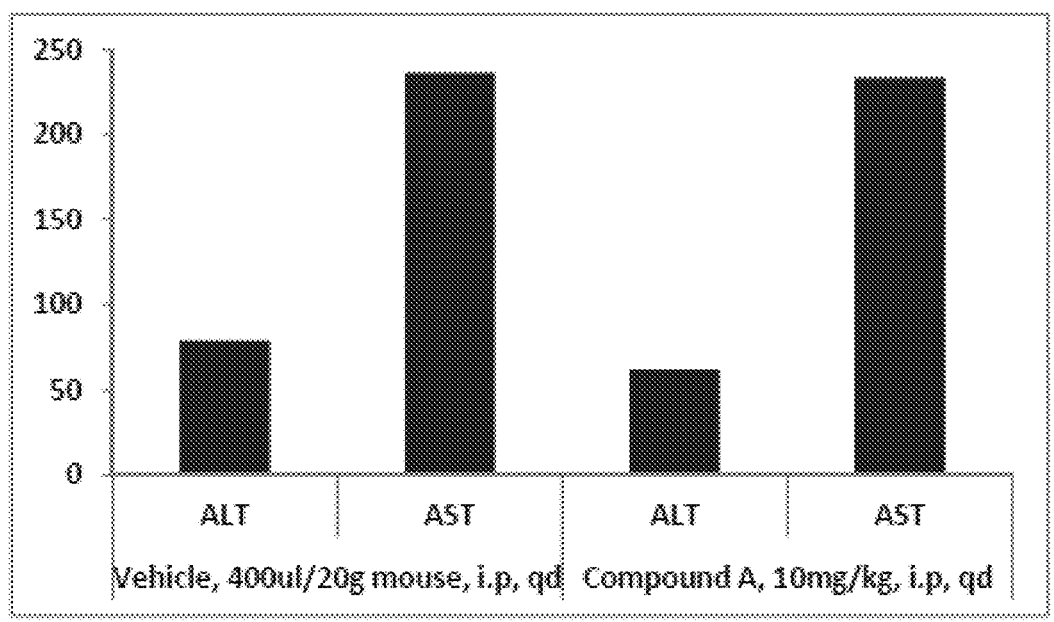
FIG. 10 is a graph depicting the comparison of ALT and AST of mice groups after treating the mice with double dose for additional 13 days after removing the outliers.

However elimination of these outlier values (yellow highlight) from the mean yielded the FIG. 10.

The details provided in this section suggested that derivative 'A' have similar profiles for liver toxicity at both 5 mg/kg and 10 mg/kg dose. With increasing dose, not much variation was observed in levels of ALT and AST. This also suggests that the mice can be treated with higher dose of derivative 'A' with no or very less toxicity.

Interpretation of Liver Function Tests (ALT and AST):

The recommendations of the Regulatory Affairs Committee of the American Society for Veterinary Clinical Pathology for the use of preclinical, clinical pathology endpoints in assessment of the potential for drug induced hepatic injury in animals and humans explains the need to perform liver function test at preclinical stage (animal model testing) during drug testing and also summarize the steps taken in this direction by various agencies in several countries around the globe. It is recommended that at least two of the markers of liver injury should be tested during preclinical testing and this list include ALT and AST. Both markers are elevated in case of drug-induced toxicity. See, Boone L, Meyer D, Cusick P, Ennulat D, Bolliger AP, Everds N, Meador V, Elliott G, Honor D, Bounous D, Jordan H. Selection and interpretation of clinical pathology indicators of hepatic injury in preclinical studies. Vet Clin Pathol. 2005 September; 34(3):182-8. PMID: 16134065, which is incorporated by reference in its entirety.

The ALT enzyme activity in the liver of humans and rats is approximately 35 U/g and 24 U/g, respectively. The respective mean serum levels are approximately 16 U/L and 38 U/L. These data suggest that increases in serum ALT levels of 2-4× in the rat are of sufficient magnitude to indicate extensive hepatocellular injury. This can serve as an indicator of potential hepatic injury in humans based on the similar concentration gradients (see Boone L. et al., VCP, 2005).

Based on reference range for rat (38 U/L), if similar reference values are considered for mice then it can be seen in FIG. 10 that derivative 'A' treated mice have mean ALT value lower than plumbagin and even lower than vehicle treated mice. This shows that derivative 'A'-1) does not induce liver toxicity when compared with plumbagin, and 2) may have the potential to reduce the toxicity linked to vehicle control. These results also point towards the role that derivative 'A' can play when given in conjunction with toxic drugs. This needs further testing but it can be interpreted from the results presented here that derivative 'A' could have the potential to reduce the liver toxicity associated with treatment drugs. The increase in AST values also show compound induced toxicity.

Figure 11:
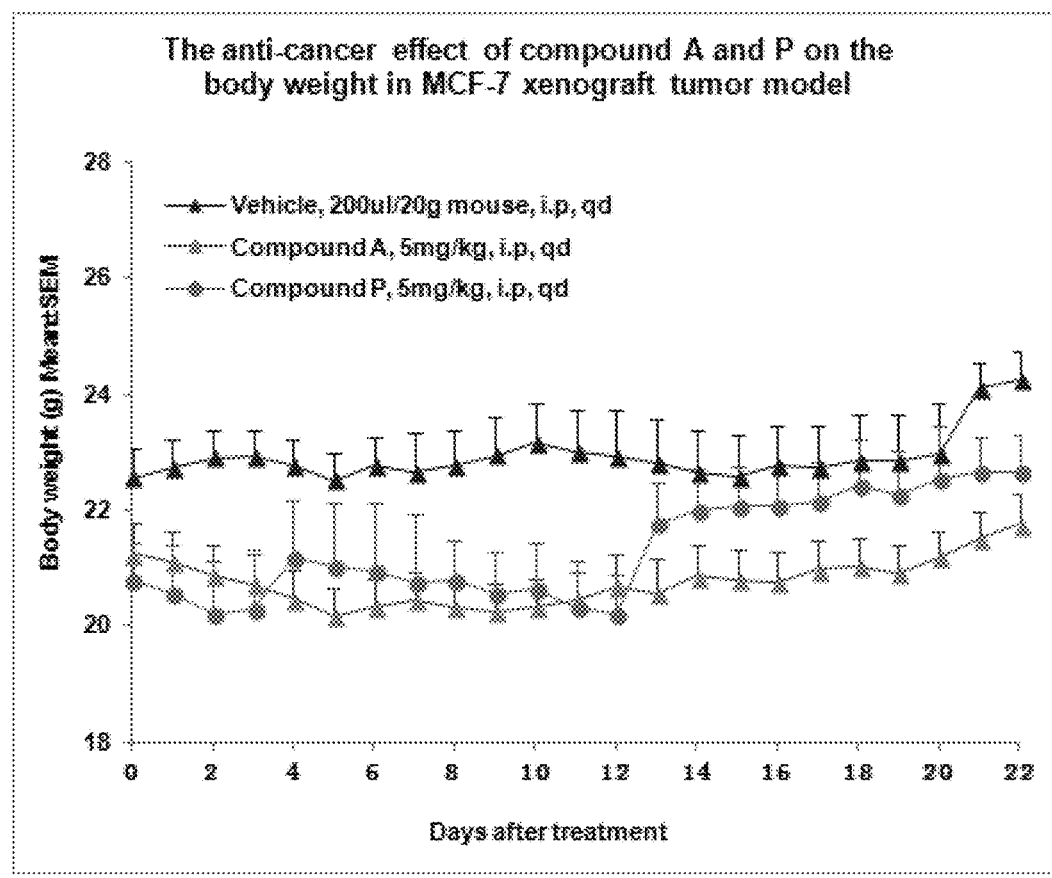
FIG. 11 is a graph depicting the body weight change curve in the course of the treatment.

The body weight of the animals was measured every second day and percent change in body weight was calculated over the period of investigation. FIG. 11 represents the changes in body weight across three groups over time.

b. Liver Tissue Harvest and H&E Staining

Figure 12:
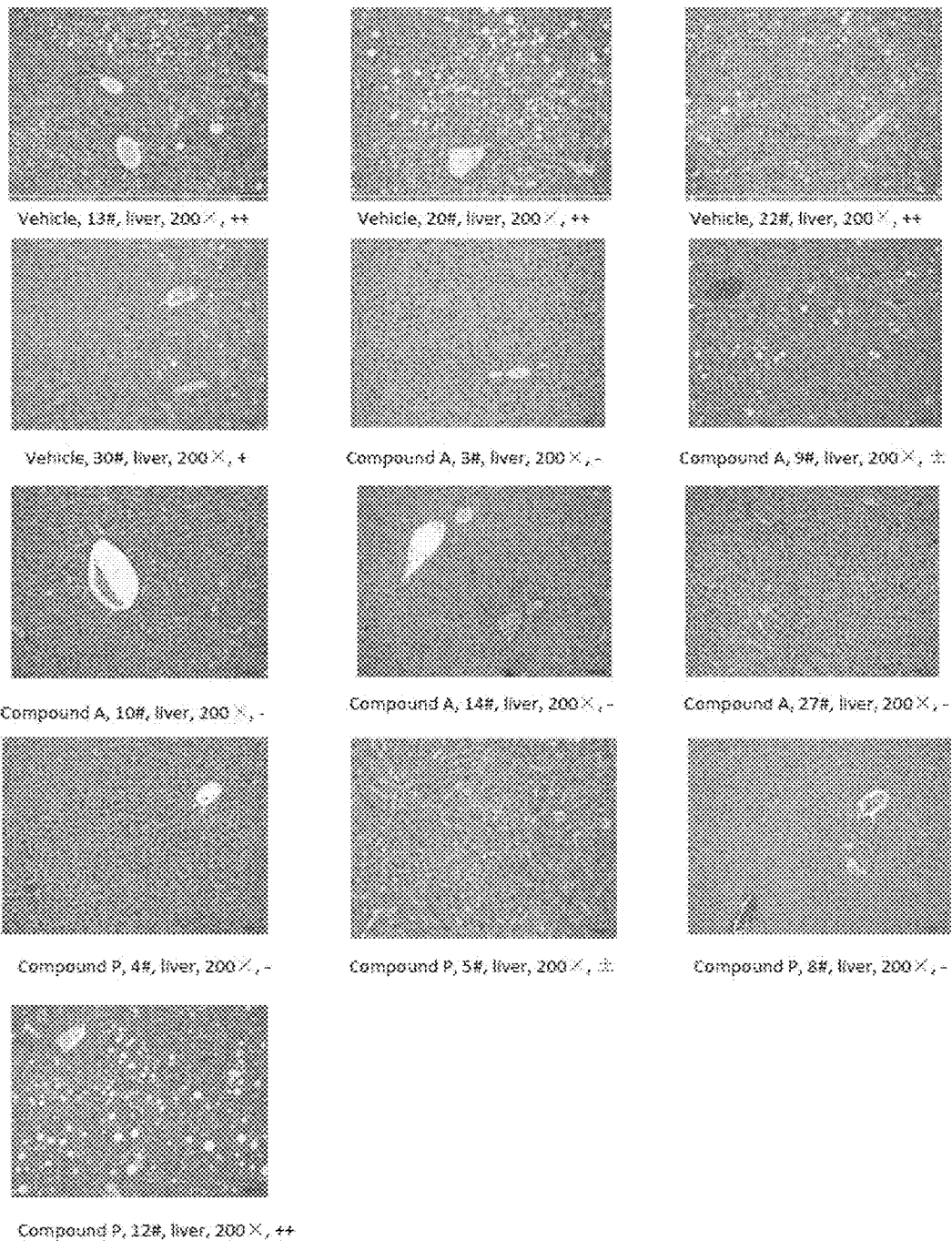
FIG. 12 is a series of photographs depicting the H&E staining of liver tissue.

The following indications were examined on the photographs for liver tissue H&E staining (FIG. 12): (1) If the liver cells produce fatty degeneration, necrosis, hepatic lobule inflammation or not; (2) If the hepaticus sinus produce dilation or hyperaemia or not; (3) If the hepaticus portal area produce the inflammation or fibrous tissue hyperplasia or not. According to pathology degree from low to high: no lesion "−", minor lesion "±", low lesion "+", middle lesion "++", high lesion "+++", highest lesion "++++". The results show that the derivative 'A' is less toxic to liver as compared to plumbagin. The vehicle control is rather showing more toxicity to liver as compared to compounds under testing.

In summary, in vivo experiments have shown that derivative 'A' has the ability to inhibit growth of tumor in vivo up to 45% at 5 mg/kg dose as compared to plumbagin at 2 mg/kg dose. A dose of 5 mg/kg of plumbagin was extremely toxic to animal and eight animals died in first few days after injecting this dose. Moreover, the toxicity of derivative 'A' is minimal as compared to plumbagin, which highlights its possible role as a future anticancer drug. No animal died with treatment of derivative 'A' and showed minimum body weight loss as well as low ALT and AST values.

Microarray Experiments

Figure 13:
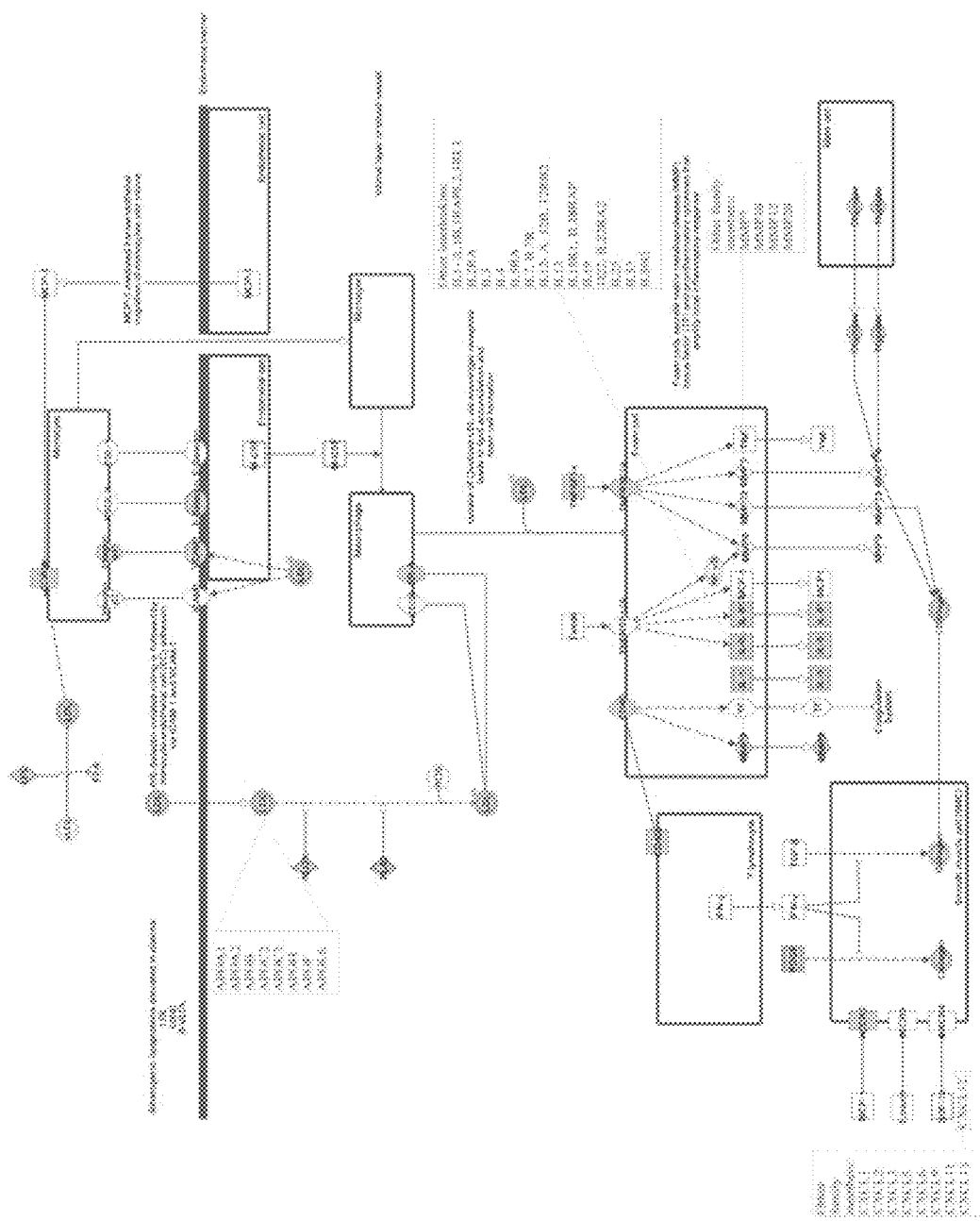
FIG. 13 is a schematic diagram of the atherosclerosis signaling pathway mapped by genes (orange outline) down-regulated after treatment with 10 μM compound A.

Microarray analysis was performed in an effort to identify the possible mechanism of action of derivative 'A'. The MCF-7 cells induced with 5 and 10 µM of derivative 'A' and plumbagin were subjected to microarray experiments and the fold-change in expression was calculated as compared to untreated samples. The lists of differentially expressed genes were mapped to pathways using Ingenuity Pathway Analysis (IPA) tool and several key pathways affected by treatment of derivative 'A' and plumbagin were identified. 'Atherosclerosis signaling' was one of the key pathways that were affected by derivative 'A' and not the plumbagin. Interestingly, not only the expression of mapped gene but also the expression of several genes in the same gene family was affected after the treatment with derivative 'A'. Examples of affected gene families are shown in presented in red in FIG. 13, which shows an atherosclerosis signaling pathway mapped by genes (orange outline) down-regulated after treatment with 10 µM compound A. LDL represents a group of apolipoproteins (APOs). In the microarray dataset, several gene families were found to be down-regulated (>2 fold) as compared to untreated samples, and as examples gene symbols of down-regulated family members of interleukins, MMPs and CXCL are shown in red in lower half of the figure.

In conclusion, derivative 'A' has emerged as a lead molecule for testing against estrogen positive breast cancer and has shown low hepatotoxicity as well as overall toxicity in nude mice model. The toxicity of derivative 'A' was determined to be even lower than vehicle control (ALT and AST markers). The possible mechanism of action identified based on the pathway mapping shows that derivative 'A' could be acting by altering the cholesterol-related mechanisms and may also prove to be useful for testing against other cholesterol associated diseases' such as atherosclerosis and Alzheimer's. The low toxicity profile of derivative 'A' highlights its possible role' as future anti-cancer drug or as an adjuvant drug to reduce the toxicity of highly toxic available chemotherapeutic' drugs.

Other embodiments are within the scope of the following claims.

We claim:

1. A method of treating breast cancer in a mammal in need comprising administering to said mammal with an effective amount of a derivative of plumbagin, or a pharmaceutically acceptable salt thereof, represented by formula (I):

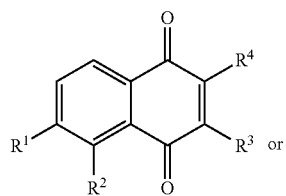
(I)

wherein $R^1$ is H;
$R^2$ is $R^a$—C(O)—O—;
$R^3$ is H;
$R^4$ is $CH_3$; and
$R^a$ is methyl, ethyl, propyl, propenyl, isopropyl, butyl, isobutyl, sec-butyl, pentyl, hexyl.

2. The method according to claim 1 wherein $R^a$ is methyl.

3. The method according to claim 1 wherein said mammal is a human.

4. The method according to claim 1 wherein said mammal is a human.

5. The method according to claim 2 wherein said mammal is a human.

6. A method of treating breast cancer in a human in need comprising administering to said human an effective amount of a derivative of plumbagin according to the chemical structure:

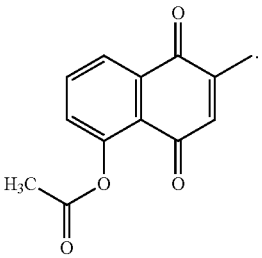 [SMILES: CC(=O)Oc1cccc2c1C(=O)C=C(C)C2=O]

* * * * *